United States Patent
Perkins et al.

(10) Patent No.: US 10,040,789 B2
(45) Date of Patent: Aug. 7, 2018

(54) 1,3,4-THIADIAZOLE COMPOUNDS AND THEIR USE IN TREATING CANCER

(71) Applicants: AstraZeneca AB, Sodertalje (SE); Cancer Research Technology Limited, London (GB)

(72) Inventors: David Robert Perkins, Macclesfield (GB); Maurice Raymond Verschoyle Finlay, Cambridge (GB); Johannes Wilhelmus Maria Nissink, Cambridge (GB); Piotr Antoni Raubo, Cambridge (GB); Peter Duncan Smith, Macclesfield (GB); Andrew Bailey, Macclesfield (GB)

(73) Assignees: AstraZeneca AB, Sodertalje (SE); Cancer Research Technology Limited, London (GB)

( * ) Notice: Subject to any disclaimer, the term of this patent is extended or adjusted under 35 U.S.C. 154(b) by 0 days.

(21) Appl. No.: 15/362,989

(22) Filed: Nov. 29, 2016

(65) Prior Publication Data
US 2017/0333429 A1    Nov. 23, 2017

Related U.S. Application Data

(60) Provisional application No. 62/260,784, filed on Nov. 30, 2015.

(51) Int. Cl.
| | | |
|---|---|---|
| C07D 417/14 | (2006.01) | |
| A61K 31/433 | (2006.01) | |
| A61K 31/501 | (2006.01) | |

(52) U.S. Cl.
CPC .......... *C07D 417/14* (2013.01); *A61K 31/433* (2013.01); *A61K 31/501* (2013.01)

(58) Field of Classification Search
CPC .................................................. C07D 417/14
See application file for complete search history.

(56) References Cited

U.S. PATENT DOCUMENTS

2014/0142081 A1    5/2014    Lemieux et al.

FOREIGN PATENT DOCUMENTS

| WO | 2013078123 A1 | 5/2013 | |
|---|---|---|---|
| WO | 2015101957 A2 | 7/2015 | |
| WO | 2015181539 A1 | 12/2015 | |
| WO | WO 2015181539 A1 * | 12/2015 | ........... C07D 417/14 |

OTHER PUBLICATIONS

Liu et al. Yale Journal of Biology and Medicine 2014, 87, 481-489.*
American Cancer Society, Can Kidney Cancer Be Prevented?, obtained from https://www.cancer.org/cancer/kidney-cancer/causes-risks-prevention/prevention.html on Sep. 13, 2017.*
American Cancer Society, Can Lung Cancer Be Prevented?, obtained from https://www.cancer.org/cancer/lung-cancer/prevention-and-early-detection/prevention.html on Sep. 13, 2017.*
American Cancer Society, Breast Cancer Risk and Prevention, obtained from https://www.cancer.org/cancer/breast-cancer/risk-and-prevention.html on Sep. 16, 2017.*
Ajit, G., et al., "Small molecule glutaminase inhibitors block glutamate release from stimulated microglia", Biochemical and Biophysical Research Communications, Jan. 1, 2014, vol. 443, No. 1, pp. 32-36.

* cited by examiner

*Primary Examiner* — Matthew P Coughlin
(74) *Attorney, Agent, or Firm* — Daniel Kopp

(57) ABSTRACT

A compound of Formula (I):

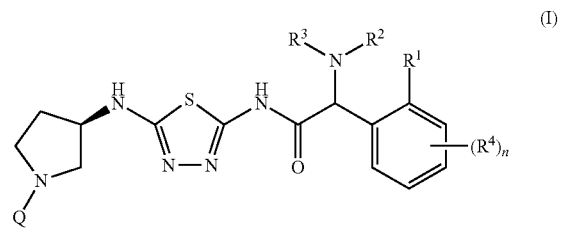

or a pharmaceutically acceptable salt thereof, is described. Q can be pyridazin-3-yl, 6-fluoropyridazin-3-yl; $R^1$ can be H; $R^2$ and $R^3$ can each independently be C1-C6 alkyl, or $R^2$ and $R^3$ taken together are —$(CH_2)_3$—; or $R^1$ and $R^2$ taken together can be —$(CH_2)_2$— and $R^3$ can be —$CH_3$; $R^4$ halo, —$CH_3$, —$OCH_3$, —$OCHF_2$, —$OCF_3$, or —CN; and n can be 0, 1, or 2. The compound of formula (I) can inhibit glutaminase, e.g., GLS1.

16 Claims, No Drawings

1,3,4-THIADIAZOLE COMPOUNDS AND THEIR USE IN TREATING CANCER

CROSS-REFERENCE TO RELATED APPLICATIONS

This application claims the benefit under 35 U.S.C. § 119(e) to U.S. Application No. 62/260,784 filed on 30 Nov. 2015, the entirety of which is hereby incorporated by reference.

TECHNICAL FIELD

The specification generally relates to substituted 1,3,4-thiadiazole compounds and pharmaceutically acceptable salts thereof. These compounds act on the glutaminase 1 enzyme ("GLS1"), and the specification therefore also relates to the use of such compounds and salts thereof to treat or prevent GLS1-mediated disease, including cancer. The specification further relates to pharmaceutical compositions comprising such compounds and salts; kits comprising such compounds and salts; methods of manufacture of such compounds and salts; intermediates useful in the manufacture of such compounds and salts; and to methods of treating GLS1 mediated disease, including cancer, using such compounds and salts.

BACKGROUND

Glutamine is the most abundant plasma amino acid and is involved in many growth promoting pathways. In particular, glutamine is involved in oxidation in the TCA cycle and in maintaining cell redox equilibrium, and also provides nitrogen for nucleotide and amino acid synthesis (Curi et al., *Front. Biosci.*, 2007, 12, 344-57; DeBerardinis and Cheng, *Oncogene* 2010, 313-324, each of which is incorporated by reference in its entirety). Many cancer cells rely on glutamine metabolism as a consequence of metabolic changes in the cell, including the Warburg effect where glycolytic pyruvate is converted to lactic acid rather than being used to create acetyl CoA (Koppenol et al., *Nature Reviews* 2011, 11, 325-337, which is incorporated by reference in its entirety). As a consequence of this reliance on glutamine metabolism, such cancer cells are sensitive to changes in exogenous glutamine levels. Furthermore, existing evidence suggests that glutaminolysis plays a key role in certain cancer types (Hensley et al., *J. Clin. Invest.* 2013, 123, 3678-3684, which is incorporated by reference in its entirety), and is associated with known oncogenic drivers such as Myc (Dang, *Cancer Res.* 2010, 70, 859-863, which is incorporated by reference in its entirety).

The first step of glutamine catabolism to glutamate is catalysed by glutaminase, which exists as two isoforms, GLS1 and GLS2, originally identified as being expressed in the kidney and liver, respectively. Kidney glutaminase (GLS1) is known to be more ubiquitously expressed than liver glutaminase (GLS2), and has 2 splice variants, KGA and the shorter GAC isoform, both of which are located in the mitochondria. (Elgadi et al., *Physiol. Genomics* 1999, 1, 51-62; Cassago et al., *Proc. Natl. Acad. Sci.* 2012, 109, 1092-1097, each of which is incorporated by reference in its entirety). GLS1 expression is associated with tumour growth and malignancy in a number of disease types (Wang et al., *Cancer Cell* 2010, 18, 207-219; van der Heuval et al., *Cancer Bio. Ther.* 2012, 13, 1185-1194, each of which is incorporated by reference in its entirety). Inhibitors of GLS1 are therefore expected to be useful in the treatment of cancer, as monotherapy or in combination with other anti-cancer agents.

SUMMARY

In one aspect, a compound of Formula (I) is provided:

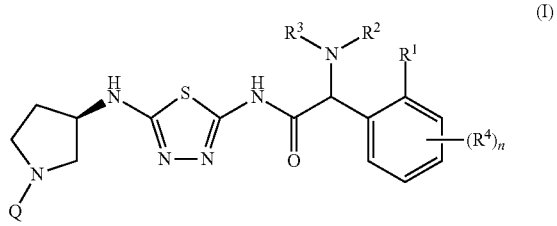

or a pharmaceutically acceptable salt thereof, where:
Q is pyridazin-3-yl, 6-fluoropyridazin-3-yl;
$R^1$ is H;
$R^2$ and $R^3$ are each independently C1-C6 alkyl, or $R^2$ and $R^3$ taken together are —$(CH_2)_3$—;
or $R^1$ and $R^2$ taken together are —$(CH_2)_2$— and $R^3$ is —$CH_3$;
$R^4$ is halo, —$CH_3$, —$OCH_3$, —$OCHF_2$, —$OCF_3$, or —CN; and
n is 0, 1, or 2.

In another aspect, a pharmaceutical composition includes a compound of Formula (I), or a pharmaceutically acceptable salt thereof, and at least one pharmaceutically acceptable diluent or carrier.

In another aspect, a compound of Formula (I), or a pharmaceutically acceptable salt thereof, for use in the treatment of cancer.

In another aspect, use of a compound of Formula (I), or a pharmaceutically acceptable salt thereof, for the manufacture of a medicament for the treatment of cancer.

In another aspect, a method for treating cancer in a warm blooded animal in need of such treatment, includes administering to the warm-blooded animal a therapeutically effective amount of a compound of Formula (I), or a pharmaceutically acceptable salt thereof.

Other aspects will be apparent from the specification and the claims.

DETAILED DESCRIPTION

Many embodiments are detailed throughout the specification and will be apparent to a reader skilled in the art. The invention is not to be interpreted as being limited to any particular embodiment(s) thereof.

A compound of Formula (I) is provided:

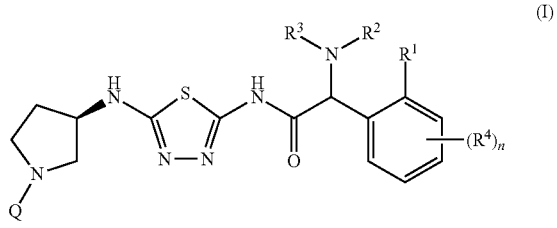

or a pharmaceutically acceptable salt thereof, where:

Q is pyridazin-3-yl, 6-fluoropyridazin-3-yl;

$R^1$ is H;

$R^2$ and $R^3$ are each independently C1-C6 alkyl, or $R^2$ and $R^3$ taken together are —(CH$_2$)$_3$—;

or $R^1$ and $R^2$ taken together are —(CH$_2$)$_2$— and $R^3$ is —CH$_3$;

$R^4$ halo, —CH$_3$, —OCH$_3$, —OCHF$_2$, —OCF$_3$, or —CN; and n is 0, 1, or 2.

Pyridazin-3-yl and 6-fluoropyridazin-3-yl rings have the following structures:

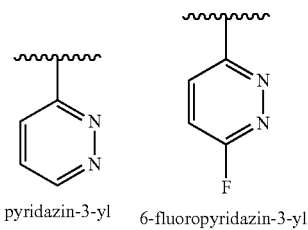 [SMILES: *c1cccnn1 ; *c1ccc(F)nn1]

pyridazin-3-yl    6-fluoropyridazin-3-yl

In some embodiments, when n is 1, then $R^4$ can be at the 3-position, i.e.:

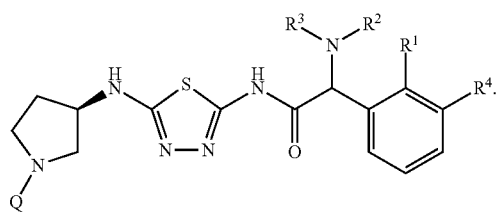

In some embodiments, when n is 1, then $R^4$ can be at the 4-position, i.e.:

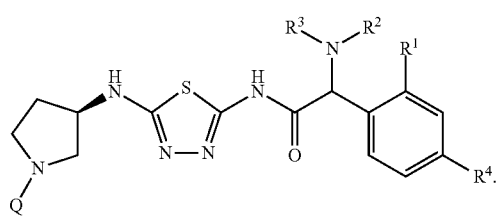

In some embodiments, when n is 2, then one instance of $R^4$ can be at the 3-position, and the other instance of $R^4$ can be at the 4-position, i.e.:

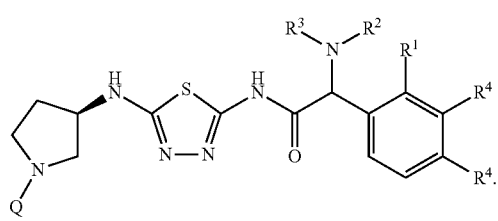

The term "pharmaceutically acceptable" is used to specify that an object (for example a salt, dosage form, diluent or carrier) is suitable for use in patients. An example list of pharmaceutically acceptable salts can be found in the *Handbook of Pharmaceutical Salts: Properties, Selection and Use*, P. H. Stahl and C. G. Wermuth, editors, Weinheim/Zürich: Wiley-VCH/VHCA, 2002, which is incorporated by reference in its entirety. A suitable pharmaceutically acceptable salt of a compound of Formula (I) is, for example, an acid-addition salt. An acid addition salt of a compound of Formula (I) may be formed by bringing the compound into contact with a suitable inorganic or organic acid under conditions known to the skilled person. An acid addition salt may be formed using, for example, an inorganic acid such as hydrochloric acid, hydrobromic acid, sulphuric acid, and phosphoric acid. An acid addition salt may also be formed using, for example, an organic acid such as trifluoroacetic acid, methanesulfonic acid, or benzenesulfonic acid.

Therefore, in one embodiment there is provided a compound of Formula (I) or a pharmaceutically acceptable salt thereof, where the pharmaceutically acceptable salt is a hydrochloric acid, hydrobromic acid, sulphuric acid, phosphoric acid, trifluoroacetic acid, methanesulfonic acid, or benzenesulfonic acid salt.

In one embodiment there is provided a compound of Formula (I) or a pharmaceutically acceptable salt thereof, where the pharmaceutically acceptable salt is a hydrochloric acid or hydrobromic acid salt.

A further suitable pharmaceutically acceptable salt of a compound of Formula (I) is a base-addition salt. A base addition salt of a compound of Formula (I) may be formed by bringing the compound into contact with a suitable inorganic or organic base under conditions known to the skilled person. A base addition salt may for example be formed using, for example, an inorganic base such as an alkali metal hydroxide (such as sodium, potassium, or lithium hydroxide) or an alkaline earth metal hydroxide (such as calcium hydroxide or magnesium hydroxide). A base addition salt may also be formed using, for example, an organic base such as methylamine, dimethylamine, trimethylamine, piperidine, morpholine, or tris-(2-hydroxyethyl) amine.

Therefore, in one embodiment there is provided a compound of Formula (I) or a pharmaceutically acceptable salt thereof, where the pharmaceutically acceptable salt is a sodium hydroxide, potassium hydroxide, lithium hydroxide, calcium hydroxide, magnesium hydroxide, methylamine, dimethylamine, trimethylamine, piperidine, morpholine, or tris-(2-hydroxyethyl)amine salt.

In one embodiment there is provided a compound of Formula (I) or a pharmaceutically acceptable salt thereof, where the pharmaceutically acceptable salt is a hydrochloric acid, hydrobromic acid, sulphuric acid, phosphoric acid, trifluoroacetic acid, methanesulfonic acid, benzenesulfonic acid, sodium hydroxide, potassium hydroxide, lithium hydroxide, calcium hydroxide, magnesium hydroxide, methylamine, dimethylamine, trimethylamine, piperidine, morpholine, or tris-(2-hydroxyethyl)amine salt.

A further embodiment provides any of the embodiments defined herein (for example the embodiment of claim 1) with the proviso that one or more specific Examples (for instance one, two or three specific Examples, or alternatively one specific Example) selected from the group consisting of Examples 1(a), 1(b), 2(a), 2(b), 3(a), 3(b), 4(a), 4(b), 5(a), 5(b), 6(a), 6(b), 7(a), 7(b), 8(a), 8(b), 9, 10, 11(a), 11(b), 12(a), 12(b), 13, 14, 15, 16, 17, and 18 is individually disclaimed.

Some values of variable groups in Formula (I) are as follows. Such values may be used in combination with any of the definitions, claims (for example claim 1), or embodiments defined herein to provide further embodiments.

Q can be pyridazin-3-yl.
Q can be 6-fluoropyridazin-3-yl.
n can be 0.
n can be 1.
n can be 2.
$R^1$ can be H.
$R^1$ can be H, n can be 1, and $R^4$ can be at the 3-position.
$R^1$ can be H, n can be 1, and $R^4$ can be 3-methyl, 3-methoxy, 3-difluoromethoxy, 3-trifluoromethoxy, or 3-cyano.
$R^1$ can be H, n can be 1, and $R^4$ can be at the 4-position.
$R^1$ can be H, n can be 1, and $R^4$ can be 4-fluoro or 4-methyl.
$R^1$ can be H, n can be 2, one instance of $R^4$ can be at the 3-position, and the other instance of $R^4$ can be at the 4-position.
$R^1$ can be H, n can be 2, and one instance of $R^4$ is 3-trifluoromethoxy, and the other instance of $R^4$ is 4-fluoro.
$R^2$ and $R^3$ can each independently be C1-C6 alkyl.
$R^2$ and $R^3$ can each independently be methyl.
$R^2$ and $R^3$ taken together can be —$(CH_2)_3$—.
$R^1$ can be H.
$R^1$ and $R^2$ taken together can be —$(CH_2)_2$— and $R^3$ can be —$CH_3$.
$R^4$ can be H.
$R^4$ can be halo.
$R^4$ can be fluoro.
$R^4$ can be —$CH_3$.
$R^4$ can be —$OCH_3$.
$R^4$ can be —$OCHF_2$.
$R^4$ can be —$OCF_3$.
$R^4$ can be —CN.

In one embodiment there is provided a compound of Formula (I), or a pharmaceutically acceptable salt thereof, where:
Q is pyridazin-3-yl or 6-fluoropyridazin-3-yl;
$R^1$ is H;
$R^2$ and $R^3$ are each independently C1-C6 alkyl, or $R^2$ and $R^3$ taken together are —$(CH_2)_3$—;
$R^4$ halo, —$CH_3$, —$OCH_3$, —$OCHF_2$, —$OCF_3$, or —CN; and
n is 0, 1, or 2.

In one embodiment there is provided a compound of Formula (I), or a pharmaceutically acceptable salt thereof, where:
Q is pyridazin-3-yl or 6-fluoropyridazin-3-yl;
$R^1$ is H;
$R^2$ and $R^3$ are each independently C1-C6 alkyl, or $R^2$ and $R^3$ taken together are —$(CH_2)_3$—;
$R^4$ halo, —$CH_3$, —$OCH_3$, —$OCHF_2$, —$OCF_3$, or —CN; and
n is 1.

In one embodiment there is provided a compound of Formula (I), or a pharmaceutically acceptable salt thereof, where:
Q is pyridazin-3-yl or 6-fluoropyridazin-3-yl;
$R^1$ is H;
$R^2$ and $R^3$ are each independently C1-C6 alkyl, or $R^2$ and $R^3$ taken together are —$(CH_2)_3$—;
$R^4$ halo, —$CH_3$, —$OCH_3$, —$OCHF_2$, —$OCF_3$, or —CN; and
n is 1, where $R^4$ is at the 3-position.

In one embodiment there is provided a compound of Formula (I), or a pharmaceutically acceptable salt thereof, where:
Q is pyridazin-3-yl or 6-fluoropyridazin-3-yl;
$R^1$ is H;
$R^2$ and $R^3$ are each independently C1-C6 alkyl;
$R^4$ halo, —$CH_3$, —$OCH_3$, —$OCHF_2$, —$OCF_3$, or —CN; and
n is 0, 1, or 2.

In one embodiment there is provided a compound of Formula (I), or a pharmaceutically acceptable salt thereof, where:
Q is pyridazin-3-yl or 6-fluoropyridazin-3-yl;
$R^1$ is H;
$R^2$ and $R^3$ are each independently C1-C6 alkyl;
$R^4$ halo, —$CH_3$, —$OCH_3$, —$OCHF_2$, —$OCF_3$, or —CN; and
n is 1, where $R^4$ is at the 3-position.

In one embodiment there is provided a compound of Formula (I), or a pharmaceutically acceptable salt thereof, where:
Q is pyridazin-3-yl or 6-fluoropyridazin-3-yl;
$R^1$ is H;
$R^2$ and $R^3$ taken together are —$(CH_2)_3$—;
$R^4$ halo, —$CH_3$, —$OCH_3$, —$OCHF_2$, —$OCF_3$, or —CN; and
n is 0, 1, or 2.

In one embodiment there is provided a compound of Formula (I), or a pharmaceutically acceptable salt thereof, where:
Q is pyridazin-3-yl or 6-fluoropyridazin-3-yl;
$R^1$ is H;
$R^2$ and $R^3$ taken together are —$(CH_2)_3$—;
$R^4$ halo, —$CH_3$, —$OCH_3$, —$OCHF_2$, —$OCF_3$, or —CN; and
n is 1, where $R^4$ is at the 3-position.

In one embodiment there is provided a compound of Formula (I), or a pharmaceutically acceptable salt thereof, where:
Q is pyridazin-3-yl or 6-fluoropyridazin-3-yl;
$R^1$ and $R^2$ taken together are —$(CH_2)_2$— and $R^3$ is —$CH_3$;
$R^4$ halo, —$CH_3$, —$OCH_3$, —$OCHF_2$, —$OCF_3$, or —CN; and
n is 0, 1, or 2.

In one embodiment there is provided a compound of Formula (I), or a pharmaceutically acceptable salt thereof, where the compound is selected from the group consisting of:

(2S)-2-(dimethylamino)-2-phenyl-N-[5-[[(3R)-1-pyridazin-3-ylpyrrolidin-3-yl]amino]-1,3,4-thiadiazol-2-yl]acetamide;

(2R)-2-(dimethylamino)-2-phenyl-N-[5-[[(3R)-1-pyridazin-3-ylpyrrolidin-3-yl]amino]-1,3,4-thiadiazol-2-yl]acetamide;

(2S)-2-(dimethylamino)-2-(4-fluorophenyl)-N-[5-[[(3R)-1-pyridazin-3-ylpyrrolidin-3-yl]amino]-1,3,4-thiadiazol-2-yl]acetamide;

(2R)-2-(dimethylamino)-2-(4-fluorophenyl)-N-[5-[[(3R)-1-pyridazin-3-ylpyrrolidin-3-yl]amino]-1,3,4-thiadiazol-2-yl]acetamide;

(2S)-2-[3-(difluoromethoxy)phenyl]-2-(dimethylamino)-N-[5-[[(3R)-1-pyridazin-3-ylpyrrolidin-3-yl]amino]-1,3,4-thiadiazol-2-yl]acetamide;

(2R)-2-[3-(difluoromethoxy)phenyl]-2-(dimethylamino)-N-[5-[[(3R)-1-pyridazin-3-ylpyrrolidin-3-yl]amino]-1,3,4-thiadiazol-2-yl]acetamide;

(2S)-2-(dimethylamino)-N-[5-[[(3R)-1-pyridazin-3-ylpyrrolidin-3-yl]amino]-1,3,4-thiadiazol-2-yl]-2-[3-(trifluoromethoxy)phenyl]acetamide;

(2R)-2-(dimethylamino)-N-[5-[[(3R)-1-pyridazin-3-ylpyrrolidin-3-yl]amino]-1,3,4-thiadiazol-2-yl]-2-[3-(trifluoromethoxy)phenyl]acetamide;

(2S)-2-(azetidin-1-yl)-2-[3-(difluoromethoxy)phenyl]-N-[5-[[(3R)-1-pyridazin-3-ylpyrrolidin-3-yl]amino]-1,3,4-thiadiazol-2-yl]acetamide;

(2R)-2-(azetidin-1-yl)-2-[3-(difluoromethoxy)phenyl]-N-[5-[[(3R)-1-pyridazin-3-ylpyrrolidin-3-yl]amino]-1,3,4-thiadiazol-2-yl]acetamide;

(2S)-2-(azetidin-1-yl)-2-(3-methoxyphenyl)-N-[5-[[(3R)-1-pyridazin-3-ylpyrrolidin-3-yl]amino]-1,3,4-thiadiazol-2-yl]acetamide;

(2R)-2-(azetidin-1-yl)-2-(3-methoxyphenyl)-N-[5-[[(3R)-1-pyridazin-3-ylpyrrolidin-3-yl]amino]-1,3,4-thiadiazol-2-yl]acetamide;

(2S)-2-(azetidin-1-yl)-N-[5-[[(3R)-1-pyridazin-3-ylpyrrolidin-3-yl]amino]-1,3,4-thiadiazol-2-yl]-2-[3-(trifluoromethoxy)phenyl]acetamide;

(2R)-2-(azetidin-1-yl)-N-[5-[[(3R)-1-pyridazin-3-ylpyrrolidin-3-yl]amino]-1,3,4-thiadiazol-2-yl]-2-[3-(trifluoromethoxy)phenyl]acetamide;

(1S)-2-methyl-N-[5-[[(3R)-1-pyridazin-3-ylpyrrolidin-3-yl]amino]-1,3,4-thiadiazol-2-yl]-3,4-dihydro-1H-isoquinoline-1-carboxamide;

(1R)-2-methyl-N-[5-[[(3R)-1-pyridazin-3-ylpyrrolidin-3-yl]amino]-1,3,4-thiadiazol-2-yl]-3,4-dihydro-1H-isoquinoline-1-carboxamide;

(2S)-2-(dimethylamino)-2-(p-tolyl)-N-[5-[[(3R)-1-pyridazin-3-ylpyrrolidin-3-yl]amino]-1,3,4-thiadiazol-2-yl]acetamide;

(2S)-2-(dimethylamino)-2-(m-tolyl)-N-[5-[[(3R)-1-pyridazin-3-ylpyrrolidin-3-yl]amino]-1,3,4-thiadiazol-2-yl]acetamide;

(2S)-2-(Azetidin-1-yl)-2-[4-fluoro-3-(trifluoromethoxy)phenyl]-N-[5-[[(3R)-1-pyridazin-3-ylpyrrolidin-3-yl]amino]-1,3,4-thiadiazol-2-yl]acetamide;

(2R)-2-(Azetidin-1-yl)-2-[4-fluoro-3-(trifluoromethoxy)phenyl]-N-[5-[[(3R)-1-pyridazin-3-ylpyrrolidin-3-yl]amino]-1,3,4-thiadiazol-2-yl]acetamide;

(2S)-2-(azetidin-1-yl)-N-[5-[[(3R)-1-(6-fluoropyridazin-3-yl)pyrrolidin-3-yl]amino]-1,3,4-thiadiazol-2-yl]-2-[3-(trifluoromethoxy)phenyl]acetamide;

(2R)-2-(azetidin-1-yl)-N-[5-[[(3R)-1-(6-fluoropyridazin-3-yl)pyrrolidin-3-yl]amino]-1,3,4-thiadiazol-2-yl]-2-[3-(trifluoromethoxy)phenyl]acetamide;

(2S)-2-(3-cyanophenyl)-2-(dimethylamino)-N-[5-[[(3R)-1-pyridazin-3-ylpyrrolidin-3-yl]amino]-1,3,4-thiadiazol-2-yl]acetamide.

In one embodiment there is provided a compound of Formula (I), or a pharmaceutically acceptable salt thereof, where the compound is selected from the group consisting of:

(2S)-2-(dimethylamino)-2-phenyl-N-[5-[[(3R)-1-pyridazin-3-ylpyrrolidin-3-yl]amino]-1,3,4-thiadiazol-2-yl]acetamide;

(2S)-2-(dimethylamino)-2-(4-fluorophenyl)-N-[5-[[(3R)-1-pyridazin-3-ylpyrrolidin-3-yl]amino]-1,3,4-thiadiazol-2-yl]acetamide;

(2R)-2-[3-(difluoromethoxy)phenyl]-2-(dimethylamino)-N-[5-[[(3R)-1-pyridazin-3-ylpyrrolidin-3-yl]amino]-1,3,4-thiadiazol-2-yl]acetamide;

(2S)-2-[3-(difluoromethoxy)phenyl]-2-(dimethylamino)-N-[5-[[(3R)-1-pyridazin-3-ylpyrrolidin-3-yl]amino]-1,3,4-thiadiazol-2-yl]acetamide;

(2S)-2-(dimethylamino)-N-[5-[[(3R)-1-pyridazin-3-ylpyrrolidin-3-yl]amino]-1,3,4-thiadiazol-2-yl]-2-[3-(trifluoromethoxy)phenyl]acetamide;

(2S)-2-(azetidin-1-yl)-2-[3-(difluoromethoxy)phenyl]-N-[5-[[(3R)-1-pyridazin-3-ylpyrrolidin-3-yl]amino]-1,3,4-thiadiazol-2-yl]acetamide;

(2S)-2-(azetidin-1-yl)-2-(3-methoxyphenyl)-N-[5-[[(3R)-1-pyridazin-3-ylpyrrolidin-3-yl]amino]-1,3,4-thiadiazol-2-yl]acetamide;

(2S)-2-(azetidin-1-yl)-N-[5-[[(3R)-1-pyridazin-3-ylpyrrolidin-3-yl]amino]-1,3,4-thiadiazol-2-yl]-2-[3-(trifluoromethoxy)phenyl]acetamide;

(1S)-2-methyl-N-[5-[[(3R)-1-pyridazin-3-ylpyrrolidin-3-yl]amino]-1,3,4-thiadiazol-2-yl]-3,4-dihydro-1H-isoquinoline-1-carboxamide;

(2S)-2-(dimethylamino)-2-(p-tolyl)-N-[5-[[(3R)-1-pyridazin-3-ylpyrrolidin-3-yl]amino]-1,3,4-thiadiazol-2-yl]acetamide;

(2S)-2-(dimethylamino)-2-(m-tolyl)-N-[5-[[(3R)-1-pyridazin-3-ylpyrrolidin-3-yl]amino]-1,3,4-thiadiazol-2-yl]acetamide;

(2S)-2-(Azetidin-1-yl)-2-[4-fluoro-3-(trifluoromethoxy)phenyl]-N-[5-[[(3R)-1-pyridazin-3-ylpyrrolidin-3-yl]amino]-1,3,4-thiadiazol-2-yl]acetamide;

(2S)-2-(azetidin-1-yl)-N-[5-[[(3R)-1-(6-fluoropyridazin-3-yl)pyrrolidin-3-yl]amino]-1,3,4-thiadiazol-2-yl]-2-[3-(trifluoromethoxy)phenyl]acetamide;

(2R)-2-(azetidin-1-yl)-N-[5-[[(3R)-1-(6-fluoropyridazin-3-yl)pyrrolidin-3-yl]amino]-1,3,4-thiadiazol-2-yl]-2-[3-(trifluoromethoxy)phenyl]acetamide; and (2S)-2-(3-cyanophenyl)-2-(dimethylamino)-N-[5-[[(3R)-1-pyridazin-3-ylpyrrolidin-3-yl]amino]-1,3,4-thiadiazol-2-yl]acetamide.

Compounds and salts described in this specification may exist in solvated forms and unsolvated forms. For example, a solvated form may be a hydrated form, such as a hemihydrate, a mono-hydrate, a di-hydrate, a tri-hydrate or an alternative quantity thereof. The present invention encompasses all such solvated and unsolvated forms of compounds of Formula (I).

Atoms of the compounds and salts described in this specification may exist in different isotopic forms. The present invention encompasses all isotopic forms of compounds of Formula (I) including an $^{11}C$ or $^{13}C$ carbon and $^{1}H$, $^{2}H$ (deuterium) or $^{3}H$ (tritium)hydrogen.

Compounds and salts described in this specification may exist as a mixture of tautomers. "Tautomers" are structural isomers that exist in equilibrium resulting from the migration of a hydrogen atom. The present invention includes all tautomers of compounds of Formula (I).

Compounds of Formula (I) can be prepared in different diastereomeric forms. The present invention includes all diastereomeric forms of the compounds of Formula (I).

In one embodiment there is provided a compound of Formula (I), or a pharmaceutically acceptable salt thereof, which is a single diastereomer being in an diastereomeric excess (% de) of ≥95%, ≥98% or ≥99%. In one embodiment, the single diastereomer is present in diastereomeric excess (% de) of ≥99%.

Compounds of Formula (I) may for example be prepared by the reaction of a compound of Formula (II):

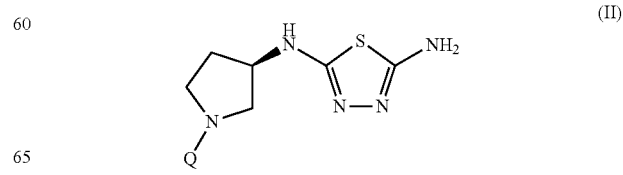

where Q is defined above, with a compound of Formula (III):

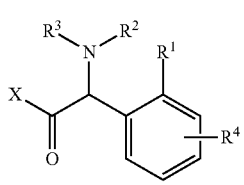
(III)

where $R^1$, $R^2$, $R^3$, and $R^4$ are defined above and X is a leaving group, such as a halogen atom (for example a chlorine atom) or a hydroxy group. The reaction is conveniently performed in a suitable solvent (for example N,N-dimethylformamide or N,N-dimethylacetamide) and in the presence of a base (for example di-isopropyl ethylamine) at a suitable temperature. Suitable temperatures include but are not limited to room temperature (from about 20° C. to about 30° C.), reduced temperature (for example from about −77° C. to about 0° C.), or elevated temperature, for example between about 80° C. and 120° C. Where X is a hydroxy group, a suitable coupling agent (for example HATU) can be used to form the amide bond.

Compounds of Formula (III), and salts thereof, are therefore useful as intermediates in the preparation of the compounds of Formula (I) and provide a further embodiment.

Compounds of Formula (II) and Formula (III) can be prepared by methods similar to those shown in the Example section.

A suitable salt of a compound of Formula (III) is a base-addition salt. A base addition salt of a compound of Formula (III) may be formed by bringing the compound into contact with a suitable inorganic or organic base under conditions known to the skilled person. Such bases need not generate pharmaceutically acceptable salts. A base addition salt may for example be formed using an inorganic base such as an alkali metal hydroxide (such as sodium, potassium, or lithium hydroxide) or an alkaline earth metal hydroxide (such as calcium hydroxide or magnesium hydroxide). A base addition salt may also be formed using an organic base such as methylamine, dimethylamine, trimethylamine, piperidine, morpholine, or tris-(2-hydroxyethyl)amine.

Therefore, in one embodiment there is provided a compound of Formula (III) or a salt thereof, where the salt is a sodium hydroxide, potassium hydroxide, lithium hydroxide, calcium hydroxide, magnesium hydroxide, methylamine, dimethylamine, trimethylamine, piperidine, morpholine, or tris-(2-hydroxyethyl)amine salt.

Compounds believed to inhibit GLS1, i.e., the compounds of Formula (I), and pharmaceutically acceptable salts thereof are expected to be useful in therapy, for example in the treatment of diseases or medical conditions mediated at least in part by GLS1, including cancer.

Where "cancer" is mentioned, this includes both non-metastatic cancer and also metastatic cancer, such that treating cancer involves treatment of both primary tumours and also tumour metastases.

In one embodiment the cancer is metastatic cancer.

In one embodiment the cancer is non-metastatic cancer.

"GLS1 inhibitory activity" refers to a decrease in the activity of GLS1 as a direct or indirect response to the presence of a compound of Formula (I), or pharmaceutically acceptable salt thereof, relative to the activity of GLS1 in the absence of compound of Formula (I), or pharmaceutically acceptable salt thereof. Such a decrease in activity may be due to the direct interaction of the compound of Formula (I), or pharmaceutically acceptable salt thereof with GLS1, or due to the interaction of the compound of Formula (I), or pharmaceutically acceptable salt thereof with one or more other factors that in turn affect GLS1 activity. For example, the compound of Formula (I), or pharmaceutically acceptable salt thereof, may decrease GLS1 by directly binding to GLS1; by causing (directly or indirectly) another factor to decrease GLS1 activity; or by (directly or indirectly) decreasing the amount of GLS1 present in the cell or organism.

The term "therapy" is intended to have its normal meaning of treating a disease or correcting or compensating for the underlying pathology. The term "therapy" also includes "prophylaxis" unless there are specific indications to the contrary. The terms "therapeutic" and "therapeutically" should be interpreted in a corresponding manner.

The term "therapeutically effective amount" refers to an amount of a compound of Formula (I) as described in any of the embodiments herein which is effective to provide therapy in a subject. In the case of cancer, the therapeutically effective amount may cause any of the changes observable or measurable in a subject as described in the definition of "therapy", "treatment" and "prophylaxis" above. For example, the effective amount can reduce the number of cancer or tumor cells; reduce the overall tumor size; inhibit or stop tumor cell infiltration into peripheral organs including, for example, the soft tissue and bone; inhibit and stop tumor metastasis; inhibit and stop tumor growth; relieve to some extent one or more of the symptoms associated with the cancer; reduce morbidity and mortality; improve quality of life; or a combination of such effects. An effective amount may be an amount sufficient to decrease the symptoms of a disease responsive to inhibition of GLS1 activity. For cancer therapy, efficacy in-vivo can, for example, be measured by assessing the duration of survival, time to disease progression (TTP), the response rates (RR), duration of response, and/or quality of life. As recognized by those skilled in the art, effective amounts may vary depending on route of administration, excipient usage, and co-usage with other agents. For example, where a combination therapy is used, the amount of the compound of Formula (I) or pharmaceutically acceptable salt described in this specification and the amount of the other pharmaceutically active agent(s) are, when combined, jointly effective to treat a targeted disorder in the animal patient. In this context, the combined amounts are in a "therapeutically effective amount" if they are, when combined, sufficient to decrease the symptoms of a disease responsive to inhibition of GLS1 activity as described above. Typically, such amounts may be determined by one skilled in the art by, for example, starting with the dosage range described in this specification for the compound of Formula (I) or pharmaceutically acceptable salt thereof and an approved or otherwise published dosage range(s) of the other pharmaceutically active compound(s). The term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease.

The term "treatment" is used synonymously with "therapy". Similarly the term "treat" can be regarded as applying therapy where "therapy" is as defined herein.

In one embodiment there is provided a pharmaceutical composition including the compound of Formula (I), or a pharmaceutically acceptable salt thereof, and at least one pharmaceutically acceptable diluent or carrier. In one embodiment, the pharmaceutical composition includes a compound of Formula (I) as a free base. In another embodiment, the pharmaceutical composition includes a a pharmaceutically acceptable salt of a compound of Formula (I).

In one embodiment there is provided a compound of Formula (I), or a pharmaceutically acceptable salt thereof, for use in therapy.

In one embodiment there is provided a compound of Formula (I), or a pharmaceutically acceptable salt thereof, for use in the treatment of cancer.

In one embodiment there is provided the use of the compound of Formula (I), or a pharmaceutically acceptable salt thereof, for the manufacture of a medicament for the treatment of cancer.

In one embodiment there is provided a compound of Formula (I), or a pharmaceutically acceptable salt thereof, for use in the treatment of a disease mediated by GLS1. In one embodiment, the disease mediated by GLS1 is cancer. In some embodiments, the cancer can be breast cancer (for example triple negative breast cancer), lung cancer (for example non-small cell lung cancer), pancreatic cancer, renal cancer, or hepatocellular cancer.

"Triple negative breast cancer" is any breast cancer that does not express, or underexpresses, the genes for the estrogen receptor, progesterone receptor and Her2/neu.

In one embodiment there is provided the use of the compound of Formula (I), or a pharmaceutically acceptable salt thereof, for the manufacture of a medicament for the treatment of a disease mediated by GLS1. In one embodiment, the disease mediated by GLS1 is cancer. In some embodiments, the cancer can be breast cancer (for example triple negative breast cancer), lung cancer (for example non-small cell lung cancer), pancreatic cancer, renal cancer, or hepatocellular cancer.

In one embodiment there is provided the use of the compound of Formula (I), or a pharmaceutically acceptable salt thereof, for the manufacture of a medicament for the treatment of cancer.

In one embodiment there is provided a method of inhibiting GLS1 which includes administering a compound of Formula (I).

In one embodiment there is provided a method for treating a disease in which inhibition of GLS1 is beneficial in a warm-blooded animal in need of such treatment, which includes administering to the warm-blooded animal a therapeutically effective amount of a compound of Formula (I), or a pharmaceutically acceptable salt thereof.

"Warm-blooded animals" include, for example, humans.

In one embodiment there is provided a method for treating cancer in a warm-blooded animal in need of such treatment, which includes administering to the warm-blooded animal a therapeutically effective amount of a compound of Formula (I), or a pharmaceutically acceptable salt thereof. In some embodiments, the cancer can be breast cancer (for example triple negative breast cancer), lung cancer (for example non-small cell lung cancer), pancreatic cancer, renal cancer, or hepatocellular cancer.

The treatment for cancer described in this specification may be applied as a sole therapy, or may involve, in addition to administration of the compound of Formula (I), conventional surgery, radiotherapy, or chemotherapy; or a combination of such additional therapies. Such conventional surgery, radiotherapy, or chemotherapy may be administered simultaneously, sequentially, or separately to treatment with the compound of Formula (I).

Therefore, in one embodiment there is provided a compound of Formula (I), or a pharmaceutically acceptable salt thereof, and at least one additional anti-tumour substance, for use in the treatment of cancer.

In one embodiment there is provided a compound of Formula (I), or a pharmaceutically acceptable salt thereof, and at least one additional anti-tumour substance for use in the simultaneous, separate or sequential treatment of cancer.

In one embodiment there is provided a compound of Formula (I), or a pharmaceutically acceptable salt thereof, for use in the treatment of cancer, where the compound of Formula (I) is administered simultaneously, separately, or sequentially with at least one additional anti-tumour substance.

In one embodiment there is provided a method of treating cancer in a warm-blooded animal who is in need of such treatment, which includes administering to the warm-blooded animal a compound of Formula (I), or a pharmaceutically acceptable salt thereof and at least one additional anti-tumour substance, wherein the amounts of the compound of Formula (I), or a pharmaceutically acceptable salt thereof, and the additional anti-tumour substance are jointly effective in producing an anti-cancer effect.

In one embodiment there is provided a method of treating cancer in a warm-blooded animal who is in need of such treatment, which includes administering to the warm-blooded animal a compound of Formula (I), or a pharmaceutically acceptable salt thereof, and simultaneously, separately or sequentially administering at least one additional anti-tumour substance to the warm-blooded animal, wherein the amounts of the compound of Formula (I), or pharmaceutically acceptable salt thereof, and the additional anti-tumour substance are jointly effective in producing an anti-cancer effect.

In any embodiment the additional anti-tumour substance is a taxane. In one embodiment the taxane is paclitaxel. In one embodiment the taxane is docetaxel.

In any embodiment the additional anti-tumour substance is a platinum therapy. In one embodiment the platinum therapy is cisplatin, oxaliplatin, or carboplatin.

According to a further embodiment there is provided a kit comprising:
a) A compound of Formula (I), or a pharmaceutically acceptable salt thereof, in a first unit dosage form;
b) A second anti-tumour substance in a second unit dosage form;
c) A container for containing the first and second unit dosage forms; and, optionally,
d) Instructions for use.

The compounds of Formula (I), and pharmaceutically acceptable salts thereof, may be administered as pharmaceutical compositions, comprising one or more pharmaceutically acceptable diluents or carriers. Accordingly, in one embodiment there is provided a pharmaceutical composition comprising a compound of Formula (I), or a pharmaceutically acceptable salt thereof, and at least one pharmaceutically acceptable diluent or carrier.

The compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular dosing), or as a suppository. The compositions may be obtained by conventional procedures using conventional pharmaceutical excipients. Thus, compositions intended for oral use may contain, for example, one or more coloring, sweetening, flavoring, and/or preservative agents.

In one embodiment there is provided a pharmaceutical composition comprising a compound of Formula (I), or a pharmaceutically acceptable salt thereof, and at least one pharmaceutically acceptable diluent or carrier, for use in therapy.

In one embodiment there is provided a pharmaceutical composition comprising a compound of Formula (I), or a pharmaceutically acceptable salt thereof, and at least one pharmaceutically acceptable diluent or carrier, for use in the treatment of cancer. In some embodiments the cancer can be breast cancer (for example triple negative breast cancer), lung cancer (for example non-small cell lung cancer), pancreatic cancer, renal cancer, or hepatocellular cancer.

The compound of Formula (I) will normally be administered to a warm-blooded animal at a unit dose within the range 5-5000 mg/m$^2$ body area of the animal, i.e., approximately 0.1-100 mg/kg, and this normally provides a therapeutically-effective dose. A unit dose form such as a tablet or capsule will usually contain, for example 1-250 mg of active ingredient. The daily dose will necessarily be varied depending upon the host treated, the particular route of administration, any therapies being co-administered, and the severity of the illness being treated. Accordingly the practitioner who is treating any particular patient may determine the optimum dosage.

EXAMPLES

The various embodiments are illustrated by the following Examples. The invention is not to be interpreted as being limited to the Examples.

During the preparation of the Examples, generally:
a) Operations were carried out at ambient temperature, i.e. in the range of about 17 to 30° C. and under an atmosphere of an inert gas such as nitrogen unless otherwise stated;
b) Evaporations were carried out by rotary evaporation or utilising Genevac equipment in vacuo and work-up procedures were carried out after removal of residual solids by filtration;
c) Flash chromatography purifications were performed on an automated Isco Combiflash Companion using Grace Resolve prepacked silica columns, and (reverse phase flash) Isco Combiflash Rf using RediSep Gold C18 columns;
d) Yields, where present, are not necessarily the maximum attainable;
e) Structures of end-products of Formula (I) were confirmed by nuclear magnetic resonance (NMR) spectroscopy, with NMR chemical shift values measured on the delta scale. Proton magnetic resonance spectra were determined using a Bruker Avance 700 (700 MHz), Bruker Avance 500 (500 MHz), Bruker 400 (400 MHz) or Bruker 300 (300 MHz) instrument; $^{19}$F NMR were determined at 282 MHz or 376 MHz; $^{13}$C NMR were determined at 75 MHz or 100 MHz; measurements were taken at around 20-30° C. unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal;
f) End-products of Formula (I) were also characterised by mass spectroscopy following liquid chromatography (LCMS), using a HPLC system based on a Waters 2790/95 LC system with a 2996 PDA and a 2000 amu ZQ single quadrupole mass spectrometer. The solvents used were A=Water, B=Acetonitrile, C=50:50 acetonitrile:water 0.1% formic acid and D=50:50 acetonitrile:water 0.1% ammonium hydroxide. At a flow rate of 1.1 mL/min 5 µL of sample was injected onto a 50×2.1 5 µm Phenomenex Gemini NX column. The gradient ran from 95% A to 95% B for 4.0 mins with a constant 5% infusion of C (for acid analysis, D is used for base analysis). The flow was held at 95% B for 0.5 mins before returning to start conditions. The Data was acquired from 150 to 850 amu in both positive and negative mode on the Mass Spectrometer and 220-320 nm on the PDA. LCMS was also performed on a UPLC system utilising a Waters Acquity Binary pump with sample manager, Acquity PDA and an SQD Mass spectrometer. The solvents used were A1=0.1% formic acid (aq), B1 0.1% formic acid in acetonitrile, A2=0.1% ammonium hydroxide (aq) and B2 0.1% ammonium hydroxide in acetonitrile. At a flow rate of 1 mL/min 1 µL of sample was injected onto a 50×2.1 1.7 um Waters BEH column (at 40° C.). The gradient ran from 97% A1 to 97% B1 over 1.30 mins before being held for 0.2 min and returning to start conditions (substitute A1 and B1 for A2 and B2 for base analysis). Data was acquired from 150-1000 amu in positive and negative ion mode on the mass spectrometer and 245-320 amu on the PDA;
g) Intermediates were not generally fully characterised and purity was assessed by thin layer chromatographic, mass spectral, HPLC and/or NMR analysis;
h) The following abbreviations have been used: h=hour(s); r.t.=room temperature (~17-30° C.); conc.=concentrated; FCC=flash column chromatography using silica; AIBN=azobisisobutyronitrile; DCM=dichloromethane; DIPEA=di-isopropyl ethylamine; DMA=N,N-dimethylacetamide; DMF=N,N-dimethylformamide; DMSO=dimethylsulfoxide; EDC=1-Ethyl-3-(3-dimethylaminopropyl)carbodiimide; Et$_2$O=diethyl ether; EtOAc=ethyl acetate; EtOH=ethanol; HATU=1-[bis(dimethylamino)methylene]-1H-1,2,3-triazolo[4,5-b]pyridinium 3-oxid hexafluorophosphate; HOBT=hydroxybenzotriazole; K$_2$CO$_3$=potassium carbonate; MeOH=methanol; MeCN=acetonitrile; MgSO$_4$=anhydrous magnesium sulphate; Na$_2$SO$_4$=anhydrous sodium sulphate; NBS=N-bromo succinimide; TFA=trifluoroacetic acid; THF=tetrahydrofuran; sat.=saturated aqueous solution.

In a number of the examples below, a diastereomeric pair of compounds is described. For example, the compounds of Example 1(a) and Example 1(b) represent a diastereomeric pair of compounds, formed as a mixture in the product of a single reaction and subsequently separated. In such examples, any assignment of stereochemistry is not absolute. By way of illustration, Examples 1(a) and 1(b) relate to the (2S,3R) and (2R,3R) diastereomers of the named compound; however, it is not intended convey that Example 1(a) is definitively assigned as the (2S,3R) diastereomer and Example 1(b) as the (2R,3R) diastereomer.

Example 1(a) and 1(b)

(2S)-2-(Dimethylamino)-2-phenyl-N-[5-[[(3R)-1-pyridazin-3-ylpyrrolidin-3-yl]amino]-1,3,4-thiadiazol-2-yl]acetamide and (2R)-2-(dimethylamino)-2-phenyl-N-[5-[[(3R)-1-pyridazin-3-ylpyrrolidin-3-yl]amino]-1,3,4-thiadiazol-2-yl]acetamide

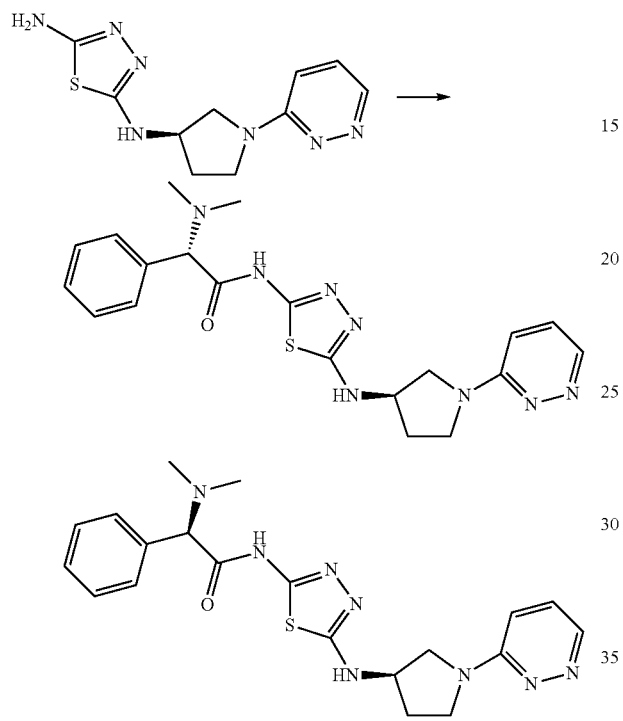

HATU (866 mg, 2.28 mmol) was added to 2-(dimethylamino)-2-phenyl-acetic acid hydrochloride (410 mg, 1.90 mmol), N'-[(3R)-1-pyridazin-3-ylpyrrolidin-3-yl]-1,3,4-thiadiazole-2,5-diamine (Intermediate 1, 500 mg, 1.90 mmol), and DIPEA (0.992 mL, 5.70 mmol) DMF (6 mL) at 0° C. The resulting solution was then stirred at ambient temperature for 2 hours. The reaction mixture was diluted with methanol (5 mL) and passed through a 20 g SCX cartridge eluting with methanol to remove non-basic impurities followed by a 3.5N solution of ammonia in methanol to bring off the product. The methanolic/ammonia washings containing product were evaporated under reduced pressure. The crude product was purified by flash silica chromatography, (elution gradient 0 to 9% (7N $NH_3$/methanol) in dichloromethane). Fractions containing product were evaporated to yield crude material. The residue was partitioned between 2-methyltetrahydrofuran and aqueous brine, the organic layer was washed with aqueous brine twice before being dried ($MgSO_4$), filtered and evaporated under reduced pressure to yield product (350 mg, 43.4%) as a gum and mixture of diastereoisomers.

The mixture was separated by chiral HPLC (C4 column, 20 micron silica, 4.6 mm diameter, 250 mm length, heptane/EtOH-MeOH 60/40). Fractions containing the desired compounds were evaporated to dryness to afford:

Example 1(a) as the first eluted isomer (solid, 128 mg, 37%). $^1$H NMR (400 MHz, DMSO, 27° C.) δ 1.99-2.09 (1H, m), 2.13 (6H, s), 2.21-2.33 (1H, m), 3.44-3.6 (3H, m), 3.73 (1H, dd), 4.06 (1H, s), 4.31-4.4 (1H, m), 6.85 (1H, dd), 7.25-7.38 (4H, m), 7.45 (2H, dd), 7.64 (1H, d), 8.47 (1H, dd), 12.13 (1H, s); m/z: $ES^+$ [M+H]$^+$ 425.

Example 1(b) as the second eluted isomer (solid, 137 mg, 39%). $^1$H NMR (400 MHz, DMSO, 27° C.) δ 2-2.1 (1H, m), 2.13 (6H, s), 2.22-2.32 (1H, m), 3.43-3.6 (3H, m), 3.73 (1H, dd), 4.06 (1H, s), 4.31-4.41 (1H, m), 6.84 (1H, dd), 7.27-7.38 (4H, m), 7.45 (2H, d), 7.64 (1H, d), 8.46 (1H, dd), 12.14 (1H, s); m/z: $ES^+$ [M+H]$^+$ 425.

Example 2(a) and 2(b)

(2S)-2-(dimethylamino)-2-(4-fluorophenyl)-N-[5-[[(3R)-1-pyridazin-3-ylpyrrolidin-3-yl]amino]-1,3,4-thiadiazol-2-yl]acetamide and (2R)-2-(dimethylamino)-2-(4-fluorophenyl)-N-[5-[[(3R)-1-pyridazin-3-ylpyrrolidin-3-yl]amino]-1,3,4-thiadiazol-2-yl]acetamide

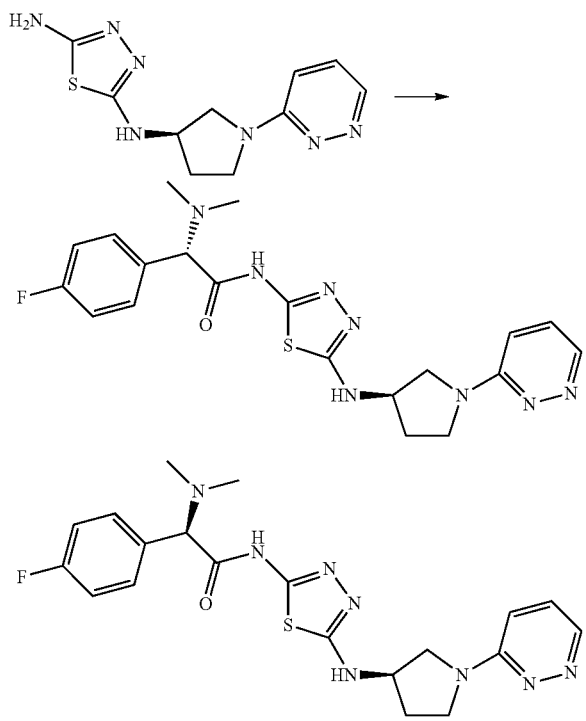

HATU (433 mg, 1.14 mmol) was added to 2-(dimethylamino)-2-(4-fluorophenyl)acetic acid hydrochloride (222 mg, 0.95 mmol), N'-[(3R)-1-pyridazin-3-ylpyrrolidin-3-yl]-1,3,4-thiadiazole-2,5-diamine (Intermediate 1, 250 mg, 0.95 mmol), and DIPEA (0.496 mL, 2.85 mmol) in DMF (3 mL) at 0° C. The resulting solution was then stirred at ambient temperature for 2 hours. The reaction mixture was diluted with methanol (5 mL) and passed through a 20 g SCX cartridge eluting with methanol to remove non-basic impurities followed by a 3.5N solution of ammonia in methanol to bring off the product. The methanolic/ammonia washings containing product were evaporated under reduced pressure. The crude product was purified by flash silica chromatography, elution gradient 0 to 9% (7N $NH_3$/methanol) in dichloromethane. Fractions containing product were evaporated to yield product. The residue was partitioned between 2-methyltetrahydrofuran and aqueous brine, the organic layer was washed twice with aqueous brine before being dried (MgSO₄), filtered and evaporated under reduced pressure to yield the crude product as a mixture of diastereoisomers.

The mixture was separated by chiral HPLC (Agilent 1100, IB column, 20 micron m silica, 4.6 mm diameter, 250 mm length, Heptane/EtOH-MeOH, 60/40 as eluent). Fractions containing the desired compounds were evaporated to dryness to afford:

Example 2(a) as the first eluted isomer (solid, 98 mg, 33%). ¹H NMR (400 MHz, DMSO, 27° C.) δ 2.01-2.1 (1H, m), 2.12 (6H, s), 2.21-2.34 (1H, m), 3.47 (1H, dd), 3.52-3.59 (2H, m), 3.73 (1H, dd), 4.07 (1H, s), 4.37 (1H, dq), 6.85 (1H, dd), 7.14-7.23 (2H, m), 7.31 (1H, dd), 7.44-7.51 (2H, m), 7.66 (1H, d), 8.46 (1H, dd), 12.18 (1H, s); m/z: ES⁺ [M+H]⁺ 443.

Example 2(b) as the as the second eluted isomer (solid, 100 mg, 33%). ¹H NMR (400 MHz, DMSO, 27° C.) δ 2-2.1 (1H, m), 2.12 (6H, s), 2.21-2.33 (1H, m), 3.46-3.58 (3H, m), 3.74 (1H, dd), 4.07 (1H, s), 4.31-4.41 (1H, m), 6.85 (1H, dd), 7.15-7.22 (2H, m), 7.32 (1H, dd), 7.48 (2H, ddd), 7.66 (1H, d), 8.47 (1H, dd), 12.17 (1H, s); m/z: ES⁺ [M+H]⁺ 443.

Example 3(a) and 3(b)

(2S)-2-[3-(difluoromethoxy)phenyl]-2-(dimethylamino)-N-[5-[[(3R)-1-pyridazin-3-ylpyrrolidin-3-yl]amino]-1,3,4-thiadiazol-2-yl]acetamide and (2R)-2-[3-(difluoromethoxy)phenyl]-2-(dimethylamino)-N-[5-[[(3R)-1-pyridazin-3-ylpyrrolidin-3-yl]amino]-1,3,4-thiadiazol-2-yl]acetamide

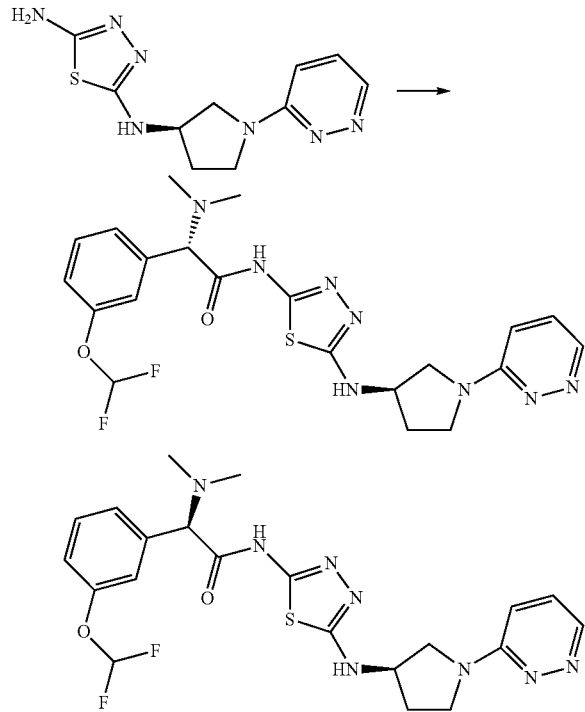

HATU (416 mg, 1.09 mmol) was added to N-[(3R)-1-pyridazin-3-ylpyrrolidin-3-yl]-1,3,4-thiadiazole-2,5-diamine (Intermediate 1, 240 mg, 0.91 mmol), 2-[3-(difluoromethoxy)phenyl]-2-(dimethylamino)acetic acid (Intermediate 9, 246 mg, 1.00 mmol) and DIPEA (0.159 mL, 0.91 mmol) in DMF (8 mL) at 21° C. under nitrogen. The resulting solution was stirred at 21° C. for 1 hour. The crude product was purified by ion exchange chromatography, using an SCX column. The desired product was eluted from the column using 1M NH₃/MeOH and pure fractions were adsorbed onto silica.

The crude product was purified by flash silica chromatography, (elution gradient 0 to 7% MeOH in DCM). Pure fractions were evaporated to dryness to afford the product as a yellow gum and mixture of diastereoisomers.

The mixture was separated by HPLC (Agilent 1100, OJ column, 20 micron m silica, 50 mm diameter, 250 mm length, MeCN/MeOH, 90/10 as eluent). Fractions containing the desired compounds were evaporated to dryness to afford:

Example 3(a) as the first eluted isomer (solid, 50 mg, 11%). ¹H NMR (400 MHz, DMSO, 30° C.) δ 2.08 (1H, m), 2.27 (1H, m), 2.49 (6H, s), 3.39-3.61 (3H, m), 3.75 (1H, m), 4.37 (1H, m), 6.95 (1H, d), 7.13-7.22 (1H, d), 7.29 (1H, s), 7.33-7.42 (4H, m), 7.48 (1H, d), 7.77 (1H, m), 8.48 (1H, d), 12.20 (1H, s); m/z: ES⁺ [M+H]⁺ 491.

Example 3(b) as the second eluted isomer (solid, 57 mg, ¹H NMR (400 MHz, DMSO, 30° C.) δ 2.08 (1H, m), 2.27 (1H, m), 2.49 (6H, s), 3.39-3.61 (3H, m), 3.75 (1H, m), 4.37 (1H, m), 6.95 (1H, d), 7.13-7.22 (1H, d), 7.29 (1H, s), 7.33-7.42 (4H, m), 7.48 (1H, d), 7.77 (1H, m), 8.48 (1H, d), 12.19 (s, 1H); m/z: ES⁺ [M+H]⁺ 491.

Example 4(a) and 4(b)

(2S)-2-(dimethylamino)-N-[5-[[(3R)-1-pyridazin-3-ylpyrrolidin-3-yl]amino]-1,3,4-thiadiazol-2-yl]-2-[3-(trifluoromethoxy)phenyl]acetamide and (2R)-2-(dimethylamino)-N-[5-[[(3R)-1-pyridazin-3-ylpyrrolidin-3-yl]amino]-1,3,4-thiadiazol-2-yl]-2-[3-(trifluoromethoxy)phenyl]acetamide

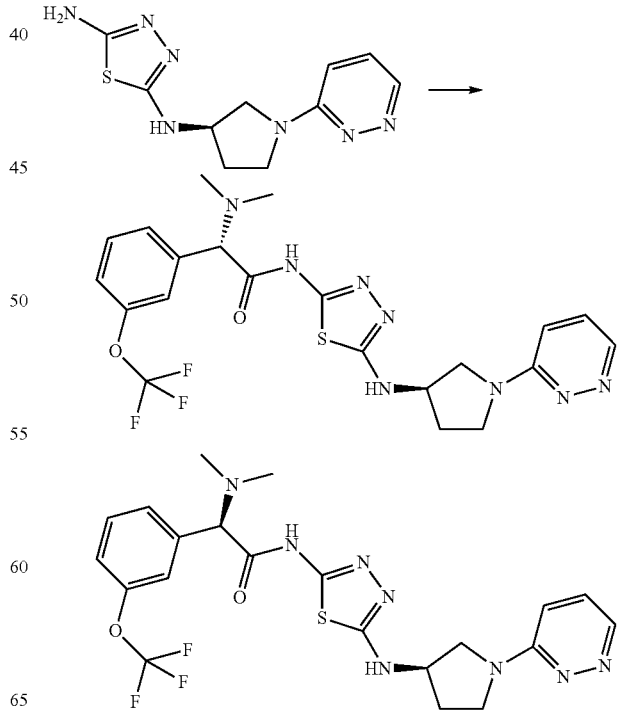

HATU (3.00 g, 7.88 mmol) was added to N-[(3R)-1-pyridazin-3-ylpyrrolidin-3-yl]-1,3,4-thiadiazole-2,5-diamine (Intermediate 1, 1.73 g, 6.57 mmol), 2-(dimethylamino)-2-[3-(trifluoromethoxy)phenyl]acetic acid (Intermediate 11, 2.248 g, 8.54 mmol) DIPEA (3.43 mL, 19.71 mmol) in DMF (30 mL) at 21° C. under nitrogen. The resulting solution was stirred at 60° C. for 1 hour. The crude product was purified by ion exchange chromatography, using an SCX column. The desired product was eluted from the column using 1M NH₃/MeOH and pure fractions were adsorbed onto silica. The crude product was purified by flash silica chromatography, (elution gradient 0 to 10% 1M NH₃/MeOH in DCM). Pure fractions were evaporated to dryness to afford a brown solid as a mixture of diastereoisomers.

The mixture was separated by HPLC (Chiral Technologies OD column, 20 m silica, 100 mm diameter, 250 mm length, 50/50 mixture of Heptane/EtOH as eluents, flow rate 450 mL/min). Fractions containing the desired compounds were evaporated to dryness to afford:

Example 4(a) as the first eluted isomer (solid, 250 mg, 7%). $^1$H NMR (400 MHz, DMSO, 30° C.) δ 1.78-1.87 (1H, m), 1.91 (6H, s), 2-2.13 (1H, m), 3.14-3.41 (3H, m), 3.51 (1H, m), 3.91 (1H, s), 4.12 (2H, m), 6.62 (1H, dd), 7.09 (2H, dd), 7.17-7.35 (3H, m), 7.40 (1H, d), 8.24 (1H, dd); m/z: ES⁺ [M+H]⁺ 509.

Example 4(b) as the second eluted isomer (solid, 285 mg, 9%). $^1$H NMR (400 MHz, DMSO, 30° C.) δ 2.08 (1H, m), 2.27 (1H, m), 2.49 (6H, s), 3.39-3.61 (3H, m), 3.75 (1H, m), 4.37 (1H, m), 6.95 (1H, d), 7.13-7.22 (1H, d), 7.29 (1H, s), 7.33-7.42 (4H, m), 7.48 (1H, d), 7.77 (1H, m), 8.48 (1H, d); m/z: ES⁺ [M+H]⁺ 509.

Example 5(a) and 5(b)

(2S)-2-(azetidin-1-yl)-2-[3-(difluoromethoxy)phenyl]-N-[5-[[(3R)-1-pyridazin-3-ylpyrrolidin-3-yl]amino]-1,3,4-thiadiazol-2-yl]acetamide and (2R)-2-(azetidin-1-yl)-2-[3-(difluoromethoxy)phenyl]-N-[5-[[(3R)-1-pyridazin-3-ylpyrrolidin-3-yl]amino]-1,3,4-thiadiazol-2-yl]acetamide

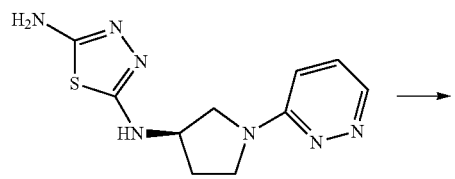

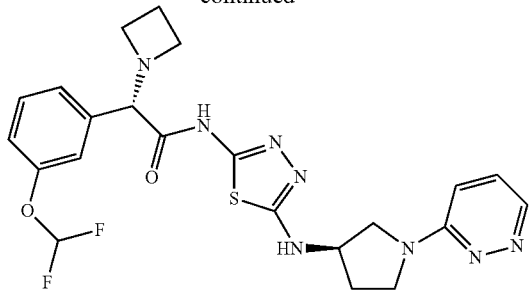

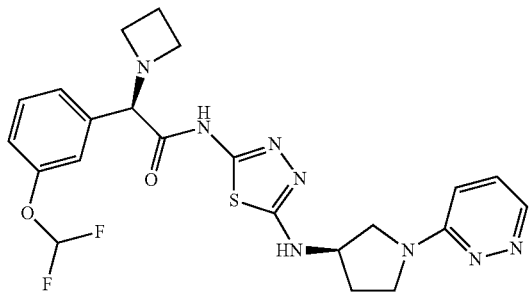

HATU (279 mg, 0.73 mmol) was added to 2-(azetidin-1-yl)-2-[3-(difluoromethoxy)phenyl]acetic acid (Intermediate 13, 145 mg, 0.56 mmol), N-[(3R)-1-pyridazin-3-ylpyrrolidin-3-yl]-1,3,4-thiadiazole-2,5-diamine (Intermediate 1, 148 mg, 0.56 mmol) and DIPEA (0.295 mL, 1.69 mmol) in N-methyl-2-pyrrolidinone (15 mL) at room temperature. The resulting solution was stirred at room temperature for 45 minutes. This solution was diluted with methanol (15 mL) and passed through a 20 g SCX-2 cartridge, flushing with methanol to remove impurities followed by a 1N solution of ammonia in methanol to bring off the product. The solvent was evaporated under reduced pressure to yield crude product. The crude product was dissolved in methanol/dichloromethane and evaporated down onto silica gel. The residue was purified by flash silica chromatography, (elution gradient 0 to 6% methanol in dichloromethane). Pure fractions were evaporated to dryness to afford the product as a gum and mixture of diastereoisomers.

The mixture was separated by HPLC (Phenomenex Lux IA column, 20 m silica, 50 mm diameter, 250 mm length, MeCN/MeOH 95/05 at 120 mL/min). Fractions containing the desired compounds were evaporated to dryness to afford:

Example 5(a) as the first eluted isomer (solid, 91 mg, 37%). $^1$H NMR (400 MHz, DMSO, 30° C.) δ 1.97-2.08 (3H, m), 2.23-2.31 (1H, m), 3.07-3.19 (4H, m), 3.46-3.6 (3H, m), 3.75 (1H, dd), 4.23 (1H, s), 4.37 (1H, dt), 6.86 (1H, dd), 7.03-7.44 (6H, m), 7.63 (1H, d), 8.48 (1H, dd), 12.00 (1H, s); m/z: ES⁺ [M+H]⁺ 503.

Example 5(b) as the second eluted isomer (solid, 43 mg, 17%). $^1$H NMR (400 MHz, DMSO, 30° C.) δ 1.97-2.11 (3H, m), 2.28 (1H, dt), 3.07-3.19 (4H, m), 3.48 (1H, dd), 3.52-3.6 (2H, m), 3.75 (1H, dd), 4.23 (1H, s), 4.34-4.42 (1H, m), 6.85 (1H, dd), 7.02-7.43 (6H, m), 7.63 (1H, d), 8.47 (1H, dd), 11.98 (1H, s); m/z: ES⁺ [M+H]⁺ 503.

Example 6(a) and 6(b)

(2S)-2-(azetidin-1-yl)-2-(3-methoxyphenyl)-N-[5-[[(3R)-1-pyridazin-3-ylpyrrolidin-3-yl]amino]-1,3,4-thiadiazol-2-yl]acetamide and (2R)-2-(azetidin-1-yl)-2-(3-methoxyphenyl)-N-[5-[[(3R)-1-pyridazin-3-ylpyrrolidin-3-yl]amino]-1,3,4-thiadiazol-2-yl]acetamide

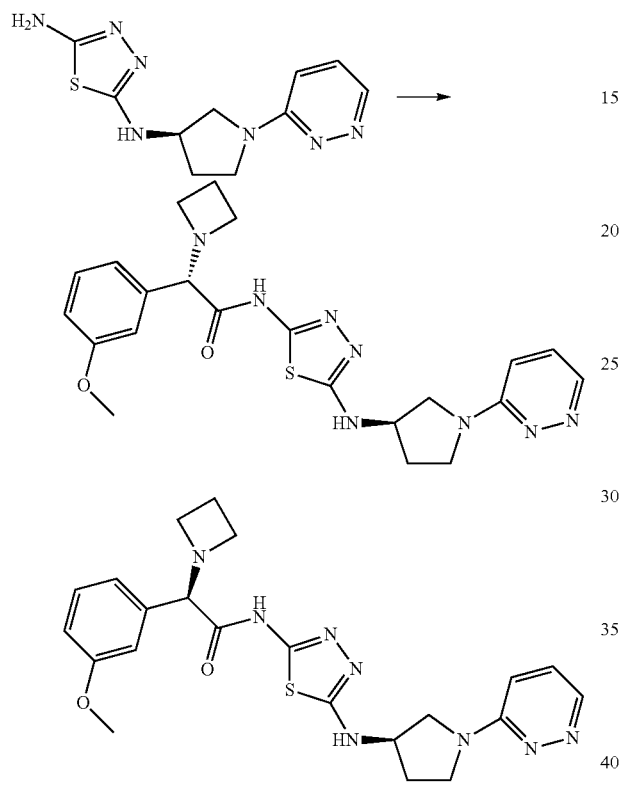

HATU (413 mg, 1.09 mmol) was added to 2-(azetidin-1-yl)-2-(3-methoxyphenyl)acetic acid (Intermediate 17, 185 mg, 0.84 mmol), N'-[(3R)-1-pyridazin-3-ylpyrrolidin-3-yl]-1,3,4-thiadiazole-2,5-diamine (Intermediate 1, 220 mg, 0.84 mmol) and DIPEA (0.438 mL, 2.51 mmol) in N-methyl-2-pyrrolidinone (15 mL) at room temperature. The resulting solution was stirred at room temperature for 45 minutes. This solution was diluted with methanol (15 mL) and passed through a 20 g SCX-2 cartridge, flushing with methanol to remove impurities followed by a 1N solution of ammonia in methanol to bring off the product. The solvent was evaporated under reduced pressure to yield crude product. The crude product was dissolved in methanol/dichloromethane and evaporated down onto silica gel. The residue was purified by flash silica chromatography, (elution gradient 0 to 12% methanol in dichloromethane). Pure fractions were evaporated to dryness to afford the product as a solid and mixture of diasteroisomers.

The mixture was separated by HPLC (Phenomenex Lux IE column, 20 m silica, 50 mm diameter, 250 mm length, eluent EtOH at 120 mL/min). Fractions containing the desired compounds were evaporated to dryness to afford:

Example 6(a) as the first eluted isomer (solid, 137 mg, 39%). $^1$H NMR (400 MHz, DMSO, 30° C.) δ 1.95-2.11 (3H, m), 2.22-2.32 (1H, m), 3.11 (4H, dq), 3.44-3.59 (3H, m), 3.71-3.77 (4H, m), 4.14 (1H, s), 4.36 (1H, dt), 6.82-6.88 (2H, m), 7.03 (1H, d), 7.06 (1H, d), 7.24 (1H, t), 7.31 (1H, dd), 7.61 (1H, d), 8.47 (1H, dd), 11.86 (1H, s); m/z: ES$^+$ [M+H]$^+$ 467.

Example 6(b) as the second eluted isomer (solid, 67 mg, 19%). $^1$H NMR (400 MHz, DMSO, 30° C.) δ 1.95-2.09 (3H, m), 2.22-2.31 (1H, m), 3.04-3.17 (4H, m), 3.45-3.59 (3H, m), 3.71-3.78 (4H, m), 4.14 (1H, s), 4.33-4.4 (1H, m), 6.83-6.88 (2H, m), 7.03 (1H, d), 7.06 (1H, s), 7.25 (1H, t), 7.31 (1H, dd), 7.61 (1H, d), 8.47 (1H, d), 11.88 (1H, s); m/z: ES$^+$ [M+H]$^+$ 467.

Example 7(a) and 7(b)

(2S)-2-(azetidin-1-yl)-N-[5-[[(3R)-1-pyridazin-3-ylpyrrolidin-3-yl]amino]-1,3,4-thiadiazol-2-yl]-2-[3-(trifluoromethoxy)phenyl]acetamide and (2R)-2-(azetidin-1-yl)-N-[5-[[(3R)-1-pyridazin-3-ylpyrrolidin-3-yl]amino]-1,3,4-thiadiazol-2-yl]-2-[3-(trifluoromethoxy)phenyl]acetamide

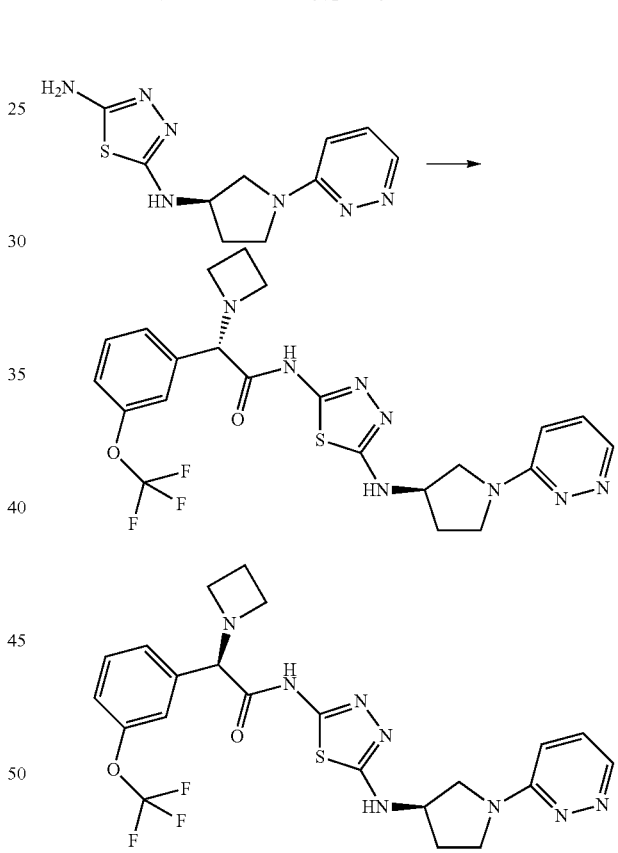

HATU (225 mg, 0.59 mmol) was added to 2-(azetidin-1-yl)-2-[3-(trifluoromethoxy)phenyl]acetic acid (Intermediate 20, 125 mg, 0.46 mmol), N-[(3R)-1-pyridazin-3-ylpyrrolidin-3-yl]-1,3,4-thiadiazole-2,5-diamine (Intermediate 1, 120 mg, 0.46 mmol) and DIPEA (0.239 mL, 1.37 mmol) in N-methyl-2-pyrrolidinone (4 mL) at room temperature. The resulting solution was stirred at room temperature for 45 minutes. This solution was diluted with methanol (15 mL) and passed through a 20 g SCX-2 cartridge, flushing with methanol to remove impurities followed by a 1N solution of ammonia in methanol to bring off the product. The solvent was evaporated under reduced pressure to yield crude product. The crude product was dissolved in methanol/dichloromethane and evaporated down onto silica gel. The residue was purified by flash silica chromatography, (elution gradient 0 to 7% methanol in dichloromethane). Pure fractions were evaporated to dryness to afford the product as a gum and a mixture of diastereoisomers.

The mixture was separated by HPLC (Chiral Technologies IA column, 20 m silica, 50 mm diameter, 250 mm length, using a 90/10 mixture of MeCN/MeOH as eluents, flow rate 120 mL/min). Fractions containing the desired compounds were evaporated to dryness to afford:

Example 7(a) as the first eluted isomer (solid, 72 mg, 38%). $^1$H NMR (400 MHz, DMSO, 30° C.) δ 1.95-2.09 (3H, m), 2.26 (1H, dt), 3.11 (4H, dq), 3.48 (1H, dd), 3.51-3.58 (2H, m), 3.74 (1H, dd), 4.26 (1H, s), 4.36 (1H, dt), 6.85 (1H, dd), 7.28-7.34 (2H, m), 7.45-7.51 (3H, m), 7.64 (1H, d), 8.47 (1H, dd), 12.09 (1H, s); m/z: ES$^+$ [M+H]$^+$ 521.

Example 7(b) as the second eluted isomer (solid, 79 mg, 42%). $^1$H NMR (400 MHz, DMSO, 30° C.) δ 1.96-2.11 (3H, m), 2.23-2.32 (1H, m), 3.05-3.16 (4H, m), 3.47 (1H, dd), 3.51-3.59 (2H, m), 3.73 (1H, dd), 4.26 (1H, s), 4.36 (1H, dq), 6.84 (1H, dd), 7.27-7.33 (2H, m), 7.44-7.5 (3H, m), 7.63 (1H, d), 8.46 (1H, dd), 12.07 (1H, s); m/z: ES$^+$ [M+H]$^+$ 521.

Example 8(a) and 8(b)

(1S)-2-methyl-N-[5-[[(3R)-1-pyridazin-3-ylpyrrolidin-3-yl]amino]-1,3,4-thiadiazol-2-yl]-3,4-dihydro-1H-isoquinoline-1-carboxamide and (1R)-2-methyl-N-[5-[[(3R)-1-pyridazin-3-ylpyrrolidin-3-yl]amino]-1,3,4-thiadiazol-2-yl]-3,4-dihydro-1H-isoquinoline-1-carboxamide

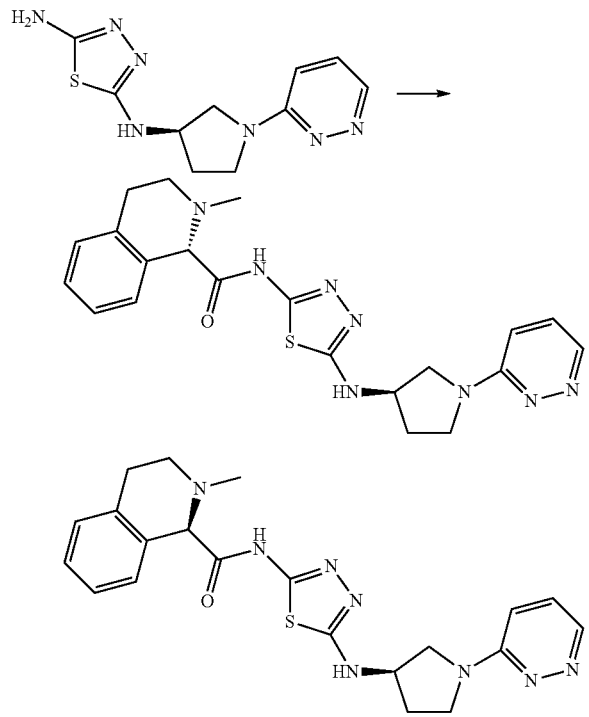

HATU (238 mg, 0.63 mmol) was added to 2-methyl-3,4-dihydro-1H-isoquinoline-1-carboxylic acid, HCl (Intermediate 24, 110 mg, 0.48 mmol), N'-[(3R)-1-pyridazin-3-ylpyrrolidin-3-yl]-1,3,4-thiadiazole-2,5-diamine (Intermediate 1, 127 mg, 0.48 mmol) and DIPEA (0.295 mL, 1.69 mmol) in N-methyl-2-pyrrolidinone (2 mL) and DMF (3 mL) at room temperature. The resulting solution was stirred at room temperature for 45 minutes. This solution was diluted with methanol (15 mL) and passed through a 20 g SCX-2 cartridge, flushing with methanol to remove impurities followed by a 1N solution of ammonia in methanol to bring off the product. The solvent was evaporated under reduced pressure to yield crude product. The crude product was purified by flash silica chromatography, (elution gradient 0 to 6% methanol in dichloromethane). Pure fractions were evaporated to dryness to afford the product as a gum and mixture of diastereoisomers.

The mixture was separated by HPLC (Phenomonex Lux C2 column, 20 m silica, 50 mm diameter, 250 mm length, using EtOH as eluents at flow rate of 120 mL/min). Fractions containing the desired compounds were evaporated to dryness to afford:

Example 8(a) as the first eluted isomer (solid, 49 mg, 43%). $^1$H NMR (400 MHz, DMSO, 30° C.) δ 2.02-2.11 (1H, m), 2.23-2.31 (1H, m), 2.37 (3H, s), 2.54-2.61 (1H, m), 2.78 (1H, dt), 2.95 (1H, dt), 3.18-3.25 (1H, m), 3.47-3.59 (3H, m), 3.75 (1H, dd), 4.35 (1H, s), 4.36-4.42 (1H, m), 6.85 (1H, dd), 7.11-7.19 (4H, m), 7.32 (1H, dd), 7.65 (1H, d), 8.47 (1H, dd), 11.95 (1H, s); m/z: ES$^+$ [M+H]$^+$ 437.

Example 8(b) as the second eluted isomer (solid, 52 mg, 46%). $^1$H NMR (400 MHz, DMSO, 30° C.) δ 2.03-2.11 (1H, m), 2.23-2.32 (1H, m), 2.37 (3H, s), 2.54-2.62 (1H, m), 2.79 (1H, dt), 2.94 (1H, dt), 3.18-3.26 (1H, m), 3.42-3.59 (3H, m), 3.74 (1H, dd), 4.35 (1H, s), 4.37-4.42 (1H, m), 6.85 (1H, dd), 7.11-7.19 (4H, m), 7.31 (1H, dd), 7.65 (1H, d), 8.47 (1H, dd), 11.97 (1H, s); m/z: ES$^+$ [M+H]$^+$ 437.

Example 9

(2S)-2-(dimethylamino)-2-(4-methylphenyl)-N-[5-[[(3R)-1-pyridazin-3-ylpyrrolidin-3-yl]amino]-1,3,4-thiadiazol-2-yl]acetamide

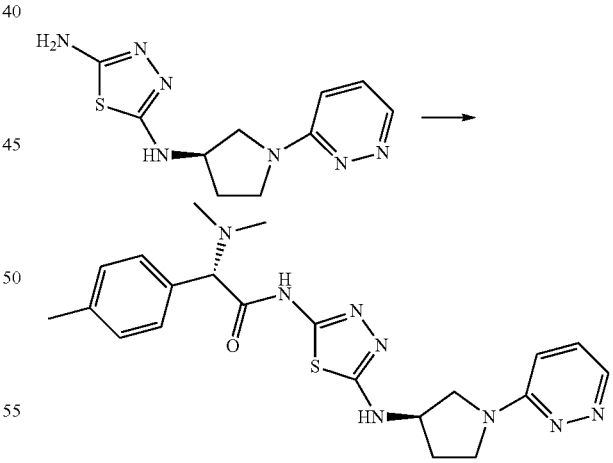

HATU (347 mg, 0.91 mmol) was added to (2S)-2-(dimethylamino)-2-(p-tolyl)acetic acid (Intermediate 26, 161 mg, 0.84 mmol), N'-[(3R)-1-pyridazin-3-ylpyrrolidin-3-yl]-1,3,4-thiadiazole-2,5-diamine (Intermediate 1, 200 mg, 0.76 mmol) and DIPEA (0.133 mL, 0.76 mmol) in DMA (7 mL) at 21° C. under nitrogen. The resulting solution was stirred at 0° C. for 45 minutes. The crude product was purified by ion exchange chromatography, using an SCX column. The desired product was eluted from the column using 1M NH$_3$/MeOH and pure fractions were evaporated to dryness to afford crude product as a gum. The crude product was purified by flash silica chromatography, (elution gradient 0 to 10% MeOH in DCM). Pure fractions were evaporated to dryness, triturated with DCM/ether and filtered to afford (2S)-2-(dimethylamino)-2-(4-methylphenyl)-N-[5-[[(3R)-1-pyridazin-3-ylpyrrolidin-3-yl]amino]-1,3,4-thiadiazol-2-yl]acetamide (109 mg, 33%) as a cream solid; $^1$H NMR (400 MHz, DMSO, 30° C.) δ 1.25 (1H, m), 2.08 (1H, dt), 2.19 (6H, s), 2.24-2.36 (4H, m), 3.48 (1H, dd), 3.54-3.65 (2H, m), 3.75 (1H, dd), 4.34-4.5 (1H, m), 6.86 (1H, dd), 7.18 (2H, d), 7.28-7.44 (3H, m), 7.66 (1H, d), 8.48 (1H, dd), 12.12 (1H, s); m/z: ES$^+$[M+H]$^+$ 439.

Example 10

(2S)-2-(dimethylamino)-2-(3-methylphenyl)-N-[5-[[(3R)-1-pyridazin-3-ylpyrrolidin-3-yl]amino]-1,3,4-thiadiazol-2-yl]acetamide

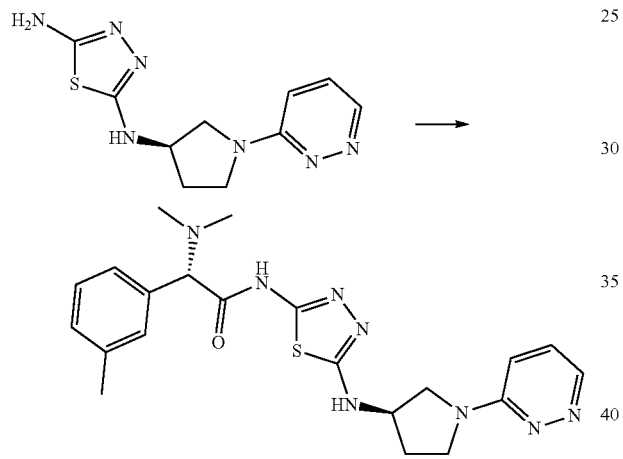

HATU (416 mg, 1.09 mmol) was added to (2S)-2-(dimethylamino)-2-(m-tolyl)acetic acid (Intermediate 27, 194 mg, 1.00 mmol), N'-[(3R)-1-pyridazin-3-ylpyrrolidin-3-yl]-1,3,4-thiadiazole-2,5-diamine (Intermediate 1, 240 mg, 0.91 mmol) DIPEA (0.159 mL, 0.91 mmol) in DMF (12 mL) at 21° C. under nitrogen. The resulting solution was stirred at 0° C. for 30 minutes. The crude product was purified by ion exchange chromatography, using an SCX column. The desired product was eluted from the column using 1M NH$_3$/MeOH and pure fractions were evaporated to dryness to afford a gum. The crude product was purified by flash silica chromatography, (elution gradient 0 to 10% methanol in DCM). Pure fractions were evaporated to dryness, triturated with DCM/ether and filtered to afford (2S)-2-(dimethylamino)-2-(m-tolyl)-N-[5-[[(3R)-1-pyridazin-3-ylpyrrolidin-3-yl]amino]-1,3,4-thiadiazol-2-yl]acetamide (91 mg, 23%) as a cream solid; $^1$H NMR (400 MHz, DMSO, 30° C.) δ 1.25 (1H, m), 2.08 (1H, dq), 2.19-2.42 (10H, m), 3.49 (1H, dd), 3.57 (2H, td), 3.75 (1H, dd), 4.29-4.46 (1H, m), 6.88 (1H, dd), 7.19 (1H, s), 7.26-7.41 (4H, m), 7.71 (1H, s), 8.48 (1H, dd), 12.30 (1H, s); m/z: ES$^+$ [M+H]$^+$439.

Example 11(a) and 11(b)

(2S)-2-(Azetidin-1-yl)-2-[4-fluoro-3-(trifluoromethoxy)phenyl]-N-[5-[[(3R)-1-pyridazin-3-ylpyrrolidin-3-yl]amino]-1,3,4-thiadiazol-2-yl]acetamide and (2R)-2-(Azetidin-1-yl)-2-[4-fluoro-3-(trifluoromethoxy)phenyl]-N-[5-[[(3R)-1-pyridazin-3-ylpyrrolidin-3-yl]amino]-1,3,4-thiadiazol-2-yl]acetamide

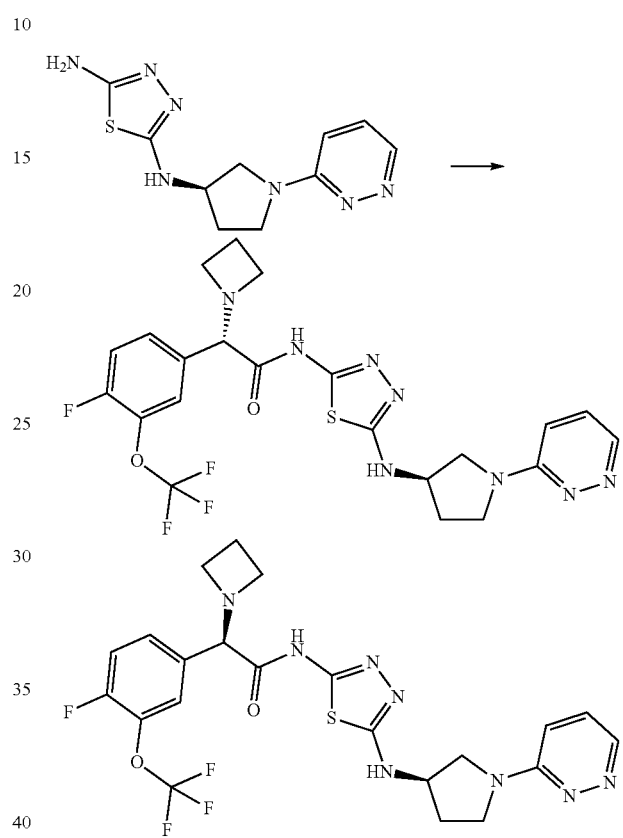

N2-[(3R)-1-pyridazin-3-ylpyrrolidin-3-yl]-1,3,4-thiadiazole-2,5-diamine (Intermediate 28, 0.09 g, 0.30 mmol) was dissolved in DMF (2 mL) under N$_2$ at r.t. [2-(azetidin-1-yl)-2-[4-fluoro-3-(trifluoromethoxy)phenyl]acetyl]oxylithium (Intermediate 1, 0.09 g, 0.307 mmol) was added, followed by DIPEA (0.08 mL, 0.46 mmol). The mixture was stirred for 5 min before addition of HATU (139.9 mg, 0.36 mmol), and then for 2 h at room temperature. The reaction mixture was diluted with MeOH (1 mL) and passed through a 5 g SCX cartridge, washed with MeOH then eluted with 2M NH$_3$ in MeOH. The basic fraction was evaporated and the residue was purified by preparative HPLC (SunFire C18 column, 5 μm, 50 mm×19 mm, flow rate 25 mL/min). Decreasingly polar ratios of water and MeCN containing 0.1% formic acid were used as a mobile phase. Pure fractions were combined, evaporated and absorbed onto a 1 g SCX cartridge which was washed with MeOH then eluted with 2 M NH$_3$ in MeOH to give 2-(azetidin-1-yl)-2-[4-fluoro-3-(trifluoromethoxy)phenyl]-N-[5-[[(3R)-1-pyridazin-3-ylpyrrolidin-3-yl]amino]-1,3,4-thiadiazol-2-yl]acetamide as an off-white solid (88 mg, 53%). The diastereomers were separated by chiral preparative HPLC (ChiralPak IA column, m silica, 50 mm diameter, 250 mm length), MeCN/MeOH 90/10 at 120 mL/min. Fractions containing the desired compounds were evaporated to dryness to give:

Example 11(a) as the first eluted isomer (35.4 mg, 21%). $^1$H NMR (400 MHz, DMSO, 30° C.) 1.97-2.1 (3H, m), 2.23-2.32 (1H, m), 3.06-3.17 (4H, m), 3.49 (1H, dd), 3.53-3.59 (2H, m), 3.75 (1H, dd), 4.26 (1H, s), 4.34-4.42 (1H, m), 6.86 (1H, d), 7.32 (1H, dd), 7.47-7.58 (2H, m), 7.64 (2H, dd), 8.48 (1H, d); m/z: ES$^+$ [M+H]$^+$ 539.

Example 11(b) as the second eluted isomer (26.9 mg, 16%). $^1$H NMR (400 MHz, DMSO, 30° C.) 1.96-2.11 (3H, m), 2.23-2.34 (1H, m), 3.07-3.17 (4H, m), 3.48 (1H, dd), 3.53-3.6 (2H, m), 3.75 (1H, dd), 4.26 (1H, s), 4.33-4.42 (1H, m), 6.85 (1H, dd), 7.32 (1H, dd), 7.47-7.57 (2H, m), 7.64 (2H, dd), 8.48 (1H, dd); m/z: ES$^+$ [M+H]$^+$ 539.

Example 12(a) and 12(b)

(2S)-2-(azetidin-1-yl)-N-[5-[[(3R)-1-(6-fluoropyridazin-3-yl)pyrrolidin-3-yl]amino]-1,3,4-thiadiazol-2-yl]-2-[3-(trifluoromethoxy)phenyl]acetamide and (2R)-2-(azetidin-1-yl)-N-[5-[[(3R)-1-(6-fluoropyridazin-3-yl)pyrrolidin-3-yl]amino]-1,3,4-thiadiazol-2-yl]-2-[3-(trifluoromethoxy)phenyl]acetamide

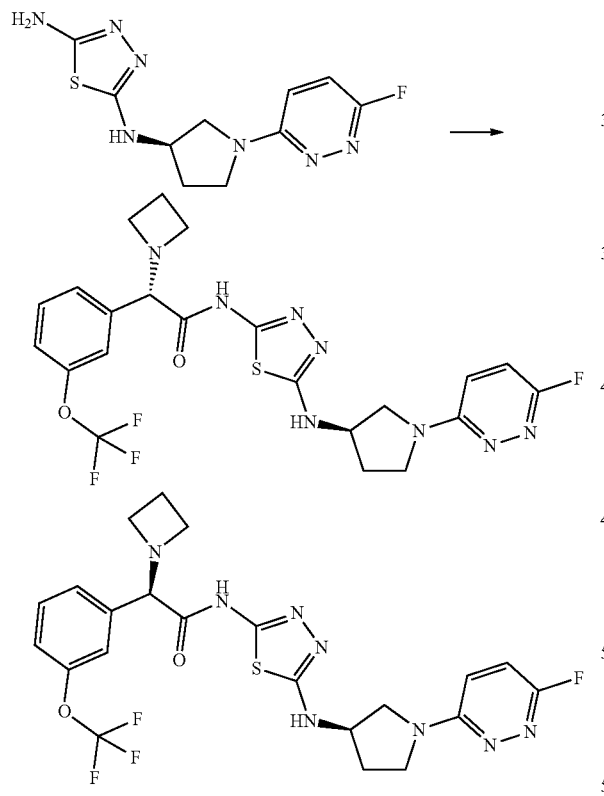

N2-[(3R)-1-(6-fluoropyridazin-3-yl)pyrrolidin-3-yl]-1,3,4-thiadiazole-2,5-diamine (Intermediate 6, 0.11 g, 0.38 mmol) and [2-(azetidin-1-yl)-2-[3-(trifluoromethoxy)phenyl]acetyl]oxylithium (Intermediate 21, 0.13 g, 0.46 mmol) were dissolved in DMF (2 mL) at r.t under N$_2$. The mixture was stirred for 5 mins before addition of DIPEA (0.34 mL, 1.943 mmol) and HATU (0.4 mL, 0.389 mmol) then at r.t. for 2 h. The crude mixture was absorbed onto a 5 g SCX column which was washed with MeOH then eluted with 2M NH$_3$ in MeOH. The basic fraction was evaporated to give an orange gum. The basic fraction was evaporated and the residue was purified by preparative HPLC (SunFire C18 column, 5 μm, 50 mm×19 mm, flow rate 25 mL/min). Decreasingly polar ratios of water and MeCN containing 0.1% formic acid were used as a mobile phase. Pure fractions were combined, evaporated and absorbed onto a 1 g SCX cartridge which was washed with MeOH then eluted with 2 M NH$_3$ in MeOH to give 2-(azetidin-1-yl)-N-[5-[[(3R)-1-(6-fluoropyridazin-3-yl)pyrrolidin-3-yl]amino]-1,3,4-thiadiazol-2-yl]-2-[3-(trifluoromethoxy)phenyl]acetamide as an off-white solid The diastereomers were separated by chiral preparative HPLC (Chiralpak IC column, 20 μm silica, 50 mm diameter, 250 mm length), heptane/EtOAc 20/80 (+0.2% TEA) at 120 ml/min. Fractions containing the desired compounds were evaporated to dryness to give:

Example 12(a) as the first eluted isomer (28.60 mg, 13%). $^1$H NMR (400 MHz, DMSO, 30° C.) 2.04-2.18 (3H, m), 2.34 (1H, dt), 3.20 (4H, dq), 3.54 (1H, dd), 3.58-3.67 (2H, m), 3.81 (1H, dd), 4.35 (1H, s), 4.4-4.48 (1H, m), 7.23 (1H, dd), 7.35-7.4 (1H, m), 7.42 (1H, dd), 7.53-7.55 (1H, m), 7.57 (2H, d), 7.71 (1H, d), 12.07 (1H, s); m/z: ES$^+$ [M+H]$^+$ 539.

Example 12(b) as the second eluted isomer (13.5 mg, 6%). $^1$H NMR (400 MHz, DMSO, 30° C.) 1.96-2.1 (3H, m), 2.28 (1H, dt), 3.13 (4H, dq), 3.46 (1H, dd), 3.51-3.59 (2H, m), 3.74 (1H, dd), 4.28 (1H, s), 4.34-4.41 (1H, m), 7.16 (1H, dd), 7.29-7.32 (1H, m), 7.34 (1H, dd), 7.47-7.49 (1H, m), 7.50 (2H, d), 7.64 (1H, d), 12.00 (1H, s); m/z: ES$^+$ [M+H]$^+$ 539.

Example 13

(2S)-2-(3-cyanophenyl)-2-(dimethylamino)-N-[5-[[(3R)-1-pyridazin-3-ylpyrrolidin-3-yl]amino]-1,3,4-thiadiazol-2-yl]acetamide

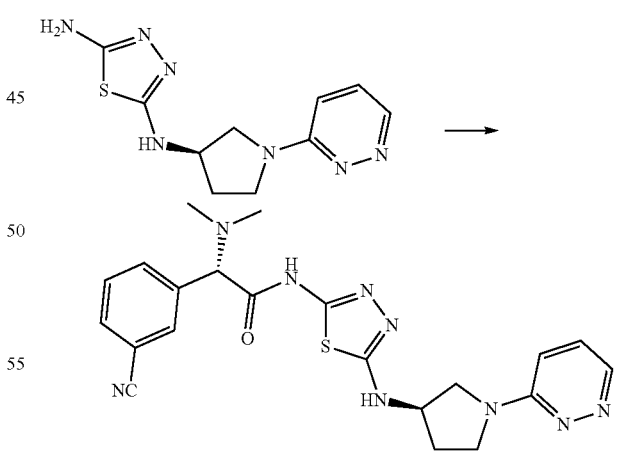

N2-[(3R)-1-pyridazin-3-ylpyrrolidin-3-yl]-1,3,4-thiadiazole-2,5-diamine (Intermediate 1, 0.09 g, 0.30 mmol) was dissolved in DMF (2 mL) under N$_2$ at r.t. (2S)-2-(3-cyanophenyl)-2-(dimethylamino)acetic acid (Intermediate 32, 0.06 g, 0.307 mmol) was added, followed by DIPEA (0.08 mL, 0.46 mmol). The mixture was stirred for 5 min before addition of HATU (139.9 mg, 0.368 mmol), and then allowed to stir at r.t. for 90 min. The reaction mixture was diluted with MeOH (1 mL) and passed through a 5 g SCX cartridge, washed with MeOH then eluted with 2M NH₃ in MeOH. The basic fraction was evaporated and purified by preparative HPLC (XBridge OBD C18 column, 5 µm, 50 mm×19 mm, flow rate 25 mL/min, decreasingly polar ratios of water and MeCN containing 0.3 mL/L NH₄OH were used as a mobile phase. Pure fractions were combined and evaporated to give (2S)-2-(3-cyanophenyl)-2-(dimethylamino)-N-[5-[[(3R)-1-pyridazin-3-ylpyrrolidin-3-yl]amino]-1,3,4-thiadiazol-2-yl]acetamide as a beige solid (43 mg, 31%). ¹H NMR (400 MHz, DMSO-d6) δ 2.09-2.02 (1H, m), 2.14 (6H, d), 2.32-2.24 (1H, m), 3.60-3.43 (3H, m), 3.74 (1H, dd), 4.17 (1H, s), 4.38 (1H, q), 6.87 (1H, ddd), 7.33 (1H, ddd), 7.60 (1H, td), 7.71 (1H, d), 7.80 (2H, ddq), 7.87 (1H, t), 8.48 (1H, dt), 12.30 (1H, s); m/z: ES⁺ [M+H]⁺ 450.

Example 14

(2R)-2-(dimethylamino)-N-[5-[[(3R)-1-pyridazin-3-ylpyrrolidin-3-yl]amino]-1,3,4-thiadiazol-2-yl]-2-[3-(trifluoromethoxy)phenyl]acetamide

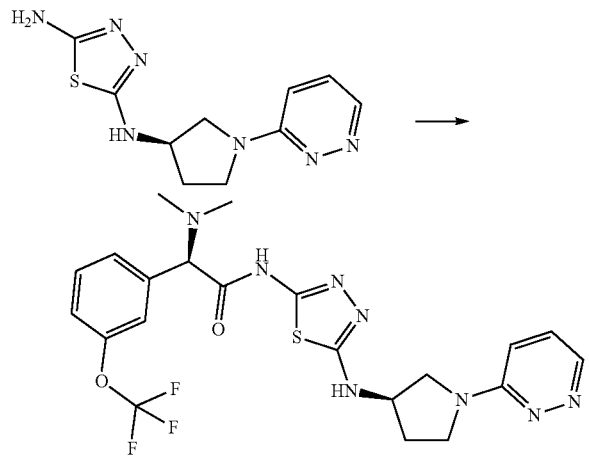

DIPEA (0.199 mL, 1.14 mmol) was added to N2-[(3R)-1-pyridazin-3-ylpyrrolidin-3-yl]-1,3,4-thiadiazole-2,5-diamine (Intermediate 1, 150 mg, 0.57 mmol), (2R)-2-(dimethylamino)-2-[3-(trifluoromethoxy)phenyl]acetic acid (Intermediate 38, 150 mg, 0.57 mmol), EDC (218 mg, 1.14 mmol) and HOBT (87 mg, 0.57 mmol) in DMF (4 mL) at 25° C. The resulting mixture was stirred at 25° C. for 16 hours. The crude product was purified by preparative HPLC (Waters XBridge Prep C18 OBD column, 5 m silica, 50 mm diameter, 150 mm length), using decreasingly polar mixtures of water and MeCN as eluents. Fractions containing the desired compound were evaporated to dryness to provide (2R)-2-(dimethylamino)-N-[5-[[(3R)-1-pyridazin-3-ylpyrrolidin-3-yl]amino]-1,3,4-thiadiazol-2-yl]-2-[3-(trifluoromethoxy)phenyl]acetamide (15 mg, 5%) as a brown solid. ¹H NMR (300 MHz, CD₃OD, 30° C.) δ 2.27-2.35 (m, 1H), 2.44-2.56 (m, 1H), 2.88 (s, 6H), 3.72-3.84 (m, 3H), 3.97-4.03 (m, 1H), 4.54-4.59 (m, 1H), 5.16 (s, 1H), 7.50-7.73 (m, 5H), 7.84-7.88 (m, 1H), 8.53 (s, 1H); m/z: ES⁻ [M−H]⁻ 507.

Example 18

(2S)-2-(dimethylamino)-N-[5-[[(3R)-1-pyridazin-3-ylpyrrolidin-3-yl]amino]-1,3,4-thiadiazol-2-yl]-2-[3-(trifluoromethoxy)phenyl]acetamide

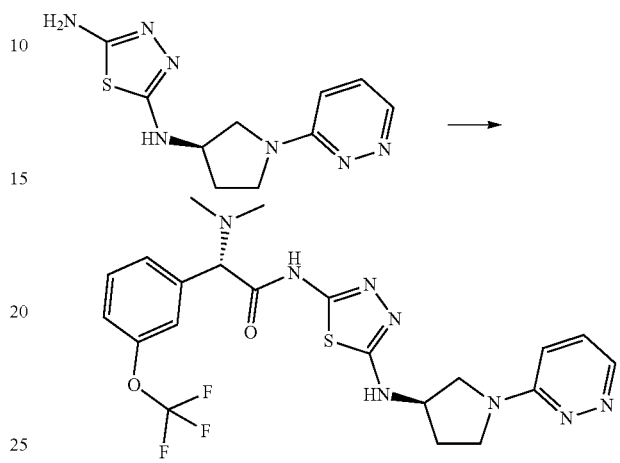

DIPEA (0.199 mL, 1.14 mmol) was added to N2-[(3R)-1-pyridazin-3-ylpyrrolidin-3-yl]-1,3,4-thiadiazole-2,5-diamine (Intermediate 1, 150 mg, 0.57 mmol), (2S)-2-(dimethylamino)-2-[3-(trifluoromethoxy)phenyl]acetic acid (Intermediate 39, 150 mg, 0.57 mmol), EDC (218 mg, 1.14 mmol) and HOBT (87 mg, 0.57 mmol) in DMF (4 mL) at 25° C. The resulting mixture was stirred at 25° C. for 16 hours. The crude product was purified by preparative HPLC (Waters XBridge Prep C18 OBD column, 5 m silica, 50 mm diameter, 150 mm length), using decreasingly polar mixtures of water and MeCN as eluents. Fractions containing the desired compound were evaporated to dryness to afford (2S)-2-(dimethylamino)-N-[5-[[(3R)-1-pyridazin-3-ylpyrrolidin-3-yl]amino]-1,3,4-thiadiazol-2-yl]-2-[3-(trifluoromethoxy)phenyl]acetamide (15 mg, 5%) as a brown solid. ¹H NMR (300 MHz, CD₃OD, 30° C.) δ 2.28-2.35 (m, 1H), 2.45-2.59 (m, 1H), 2.86 (s, 6H), 3.69-3.77 (m, 1H), 3.77-3.84 (m, 2H), 3.95-4.01 (m, 1H), 4.56-4.58 (m, 1H), 5.12 (s, 1H), 7.49-7.69 (m, 5H), 7.79-7.84 (m, 1H), 8.51 (d, 1H); m/z: ES⁻ [M−H]⁻ 507.

Additional Examples

The compounds of the following Examples were prepared in a similar fashion to the Examples above.

| Example no. | Name | MS data |
| --- | --- | --- |
| 14 | (2R)-2-(dimethylamino)-N-[5-[[(3R)-1-pyridazin-3-ylpyrrolidin-3-yl]amino]-1,3,4-thiadiazol-2-yl]-2-[3-(trifluoromethoxy)phenyl]acetamide | m/z (ES+), [M − H]− = 507 |
| 15 | (2R)-2-(dimethylamino)-2-(4-methoxyphenyl)-N-[5-[[(3R)-1-pyridazin-3-ylpyrrolidin-3-yl]amino]-1,3,4-thiadiazol-2-yl]acetamide | m/z (ES+), [M + H]+ = 455 |
| 16 | (2S)-2-(dimethylamino)-2-(4-methoxyphenyl)-N-[5-[[(3R)-1-pyridazin-3-ylpyrrolidin-3-yl]amino]-1,3,4-thiadiazol-2-yl]acetamide | m/z (ES+), [M + H]+ = 455 |
| 17 | (2S)-2-(dimethylamino)-2-(o-tolyl)-N-[5-[[(3R)-1-pyridazin-3-ylpyrrolidin-3-yl]amino]-1,3,4-thiadiazol-2-yl]acetamide | m/z (ES+), [M + H]+ = 439 |

| Example no. | Name | MS data |
|---|---|---|
| 18 | (2S)-2-(dimethylamino)-N-[5-[[(3R)-1-pyridazin-3-ylpyrrolidin-3-yl]amino]-1,3,4-thiadiazol-2-yl]-2-[3-(trifluoromethoxy)phenyl]acetamide | m/z (ES+), [M − H]− = 507 |

Intermediate 1

N'-[(3R)-1-Pyridazin-3-ylpyrrolidin-3-yl]-1,3,4-thiadiazole-2,5-diamine

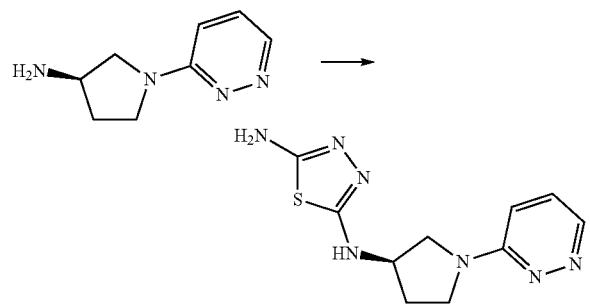

Into a 1 L round-bottom flask was placed a solution of (3R)-1-pyridazin-3-ylpyrrolidin-3-amine dihydrochloride (Intermediate 2, 10.5 g, 44.29 mmol) in DMF (400 mL), 5-bromo-1,3,4-thiadiazol-2-amine (7.94 g, 44.10 mmol) and DIPEA (17.07 g, 132.08 mmol). The solution was stirred for 4 h at 80° C. The resulting mixture was concentrated under vacuum. The crude product was purified by re-crystallization from ethanol/EtOAc to give N-[(3R)-1-pyridazin-3-ylpyrrolidin-3-yl]-1,3,4-thiadiazole-2,5-diamine as a light yellow solid (11 g, 94%). 1H NMR (500 MHz, DMSO-d6, 30° C.) δ 2.04 (1H, td), 2.22-2.31 (1H, m), 3.43-3.62 (3H, m), 3.72 (1H, dd), 4.28 (1H, dq), 6.27 (2H, s), 6.86 (1H, dd), 7.07 (1H, d), 7.33 (1H, dd), 8.48 (1H, dd). m/z: ES+ [M+H]+ 264.28.

Intermediate 1 was also prepared on a large scale according to the following alternative procedure:

(R)-1-(Pyridazin-3-yl)pyrrolidin-3-amine (Intermediate 3, free base form, 25.5 g, 150.63 mmol) and 5-bromo-1,3,4-thiadiazol-2-amine (29.8 g, 165.70 mmol) with DIPEA (39.4 mL, 225.95 mmol) was agitated as a slurry in MeOH (200 mL) at 45° C. The slurry was cooled to 20° C. and the solid isolated by vacuum filtration. 50 ml MeOH was used as a displacement wash of the filter cake and it was then dried overnight in the vacuum oven at 40° C. Intermediate 1 (32.9 g, 83%) was obtained as a free flowing beige powder.

Intermediate 2

(3R)-1-Pyridazin-3-ylpyrrolidin-3-amine dihydrochloride

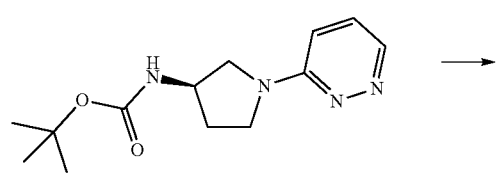

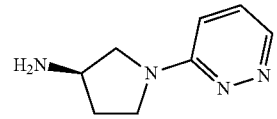

Into a 1 L round-bottom flask was placed a solution of tert-butyl N-[(3R)-1-pyridazin-3-ylpyrrolidin-3-yl]carbamate (Intermediate 4, 20 g, 75.66 mmol) in dioxane (200 mL) and concentrated HCl (100 mL). The solution was stirred for 30 mins at r.t. The resulting mixture was concentrated under vacuum. The crude product was re-crystallized from MeOH/EtOAc in the ratio of 1:2. This resulted in (3R)-1-pyridazin-3-ylpyrrolidin-3-amine dihydrochloride as an off-white solid (13.4 g, 75%). 1H NMR (300 MHz, DMSO-d6, 26° C.) δ 2.25-2.43 (2H, m), 3.66-3.74 (1H, m), 3.78-3.90 (3H, m), 4.02-4.10 (1H, m), 7.75 (1H, d), 7.94 (1H, dd), 8.66 (1H, d), 8.77-8.98 (3H, brm). m/z: ES+ [M+H]+ 165.

Intermediate 3 (free base form) was also prepared according to the following procedure:

tert-butyl N-[(3R)-1-(6-Chloropyridazin-3-yl)pyrrolidin-3-yl]carbamate (Intermediate 5, 20 g, 107.38 mmol) in pyridine (400 mL) was mixed with palladium hydroxide on carbon (Pearlman's Catalyst, 27.5 g, 25.84 mmol) and 1-methyl-1,4-cyclohexadiene (31.0 ml, 276.13 mmol) in MeOH (1375 mL). The reaction mixture was then heated to 65° C. for 90 minutes. With complete conversion observed, the reaction was cooled back to ambient temperature and the catalyst removed by filtration. 3M HCl in MeOH (184 mL, 552.27 mmol) was then charged to the reaction mixture, and the solution heated to 65° C. for 1 h. With complete conversion observed, the reaction solution was cooled back to ambient and passed through 10×50 g SCX columns which had been pre-eluted with MeOH. The compound was released from the SCX using 1M NH3 in MeOH. The resulting solution was diluted with toluene (1 L) and concentrated to dryness via rotary evaporation to give a free flowing solid. (3R)-1-pyridazin-3-ylpyrrolidin-3-amine was isolated at a strength of 97% w/w as the free base.

Intermediate 4 tert-Butyl N-[(3R)-1-pyridazin-3-ylpyrrolidin-3-yl]carbamate

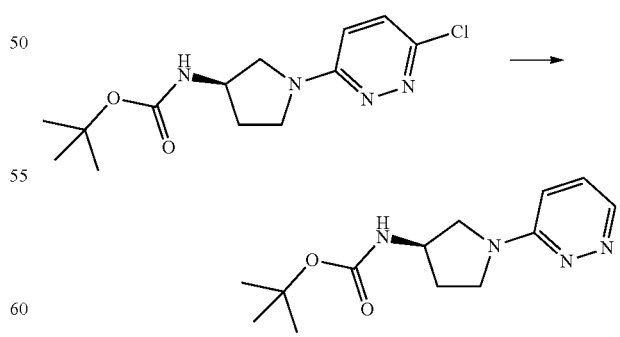

Into a 2 L round-bottom flask was placed a solution of tert-butyl N-[(3R)-1-(6-chloropyridazin-3-yl)pyrrolidin-3-yl]carbamate (Intermediate 5, 23 g, 76.98 mmol) in MeOH (800 mL) and Palladium on carbon (2 g). The system was purged and maintained with Hydrogen gas. The resulting solution was stirred for 4 h at r.t. The solids were filtered out. The resulting mixture was concentrated under vacuum to give tert-butyl N-[(3R)-1-pyridazin-3-ylpyrrolidin-3-yl]carbamate (20 g, 84%) as a yellow solid. ¹H NMR (300 MHz, CDCl₃, 24° C.) δ 1.44 (9H, s), 2.25-2.35 (2H, m), 3.48-3.56 (1H, m), 3.70-4.10 (3H, m), 4.35-4.42 (1H, m), 7.26-7.32 (1H, m), 7.70-7.75 (1H, m), 8.53-8.55 (1H, m). m/z: ES⁺ [M+H]⁺ 265.

Intermediate 5 tert-Butyl N-[(3R)-1-(6-chloropyridazin-3-yl)pyrrolidin-3-yl]carbamate

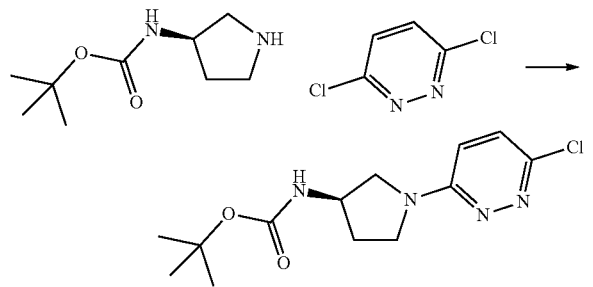

Into a 1 L round-bottom flask was placed a solution of tert-butyl N-[(3R)-pyrrolidin-3-yl]carbamate (20 g, 107.38 mmol) in pyridine (400 mL) and 3,6-dichloropyridazine (16 g, 107.40 mmol). The resulting solution was heated to reflux for overnight. The resulting mixture was concentrated under vacuum. The crude product was purified by re-crystallization from ethanol/Et₂O in the ratio of 1:3 to give tert-butyl N-[(3R)-1-(6-chloropyridazin-3-yl)pyrrolidin-3-yl]carbamate (23 g, 72%) as a yellow solid.

¹H NMR (400 MHz, CDCl₃, 30° C.) δ 1.45 (9H, s), 2.02 (1H, dq), 2.31 (1H, td), 3.41 (1H, dd), 3.54-3.70 (2H, m), 3.78 (1H, dd), 4.37 (1H, s), 4.76 (1H, s), 6.61 (1H, d), 7.17 (1H, d). m/z: ES⁺ [M+H]⁺ 299.

Intermediate 6

N2-[(3R)-1-(6-Fluoropyridazin-3-yl)pyrrolidin-3-yl]-1,3,4-thiadiazole-2,5-diamine

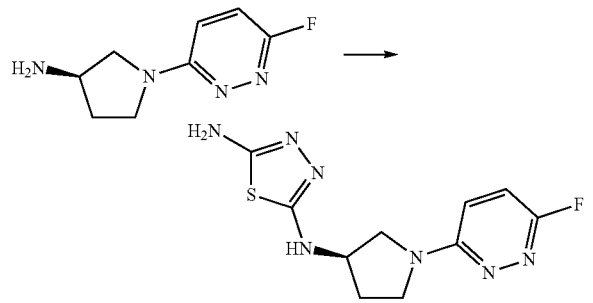

DIPEA (3.48 mL, 19.96 mmol) was added to 5-bromo-1,3,4-thiadiazol-2-amine (1.797 g, 9.98 mmol) and (3R)-1-(6-fluoropyridazin-3-yl)pyrrolidin-3-amine (Intermediate 7, 2 g, 10.98 mmol) in anhydrous DMF (40 mL) at r.t. The resulting solution was stirred at 80° C. for 4 h. The crude product was purified by ion exchange chromatography, using an SCX column. The desired product was eluted from the column using 1M NH₃ in MeOH and pure fractions were evaporated to dryness to afford N2-[(3R)-1-(6-fluoropyridazin-3-yl)pyrrolidin-3-yl]-1,3,4-thiadiazole-2,5-diamine (2.9 g, 103%) as a brown solid. ¹H NMR (400 MHz, DMSO-d6, 30° C.) δ 1.90-2.12 (1H, m), 2.23 (1H, dtd), 3.42 (1H, dd), 3.47-3.61 (2H, m), 3.69 (1H, dd), 4.25 (1H, dq), 6.25 (2H, s), 7.04 (1H, d), 7.14 (1H, dd), 7.33 (1H, dd). m/z: ES⁺ [M+H]⁺ 282.

Intermediate 7

(3R)-1-(6-Fluoropyridazin-3-yl)pyrrolidin-3-amine

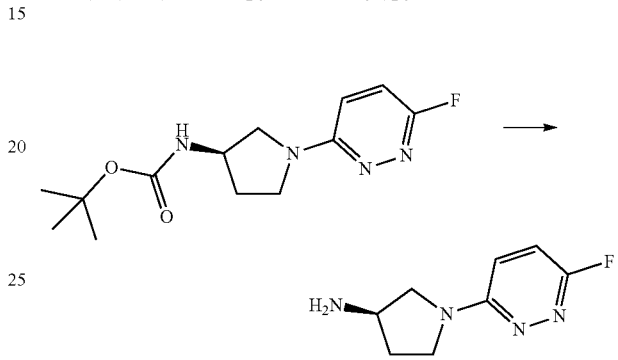

tert-Butyl N-[(3R)-1-(6-fluoropyridazin-3-yl)pyrrolidin-3-yl]carbamate (Intermediate 8, 6 g, 21.25 mmol) was added to DCM (70 mL) and TFA (14.00 mL) at 25° C. The resulting solution was stirred at 25° C. for 4 h. The crude product was purified by ion exchange chromatography, using an SCX column. The desired product was eluted from the column using 1M NH₃ in MeOH and pure fractions were evaporated to dryness to afford (3R)-1-(6-fluoropyridazin-3-yl)pyrrolidin-3-amine (2.0 g, 52%) as a pale yellow gummy solid. ¹H NMR (400 MHz, DMSO-d6, 30° C.) δ 1.55-1.83 (1H, m), 1.98-2.13 (1H, m), 2.89-3.14 (1H, m), 3.29-3.43 (1H, m), 3.54 (3H, ddt), 7.06 (1H, dd), 7.30 (1H, dd). m/z: ES⁺ [M+H]⁺ 183.

Intermediate 8 tert-butyl N-[(3R)-1-(6-Fluoropyridazin-3-yl)pyrrolidin-3-yl]carbamate

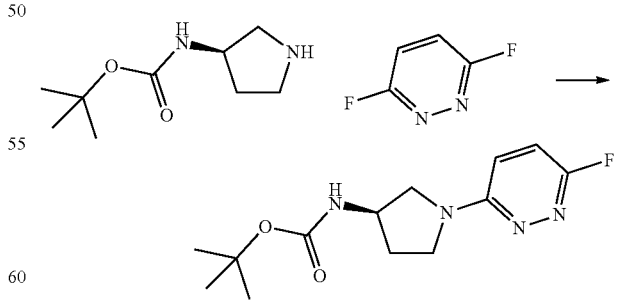

A mixture of 3,6-difluoropyridazine (6.06 g, 52.21 mmol) tert-butyl N-[(3R)-pyrrolidin-3-yl]carbamate (9.72 g, 52.21 mmol), DIPEA (22.80 mL, 130.53 mmol) and n-butanol (140 mL) was stirred at 130° C. for 10 h. The reaction mixture was diluted with EtOAc (750 mL), and washed twice with water (150 mL). The organic layer was dried over Na$_2$SO$_4$, filtered and evaporated to afford crude product. This was then dissolved in DCM and the crude product was purified by FCC (SiO$_2$, 30-65% EtOAc in heptanes). Pure fractions were evaporated to dryness to afford tert-butyl N-[(3R)-1-(6-fluoropyridazin-3-yl)pyrrolidin-3-yl]carbamate (15 g, 102%) as a cream solid. $^1$H NMR (400 MHz, CDCl$_3$, 30° C.) δ 1.46 (9H, s), 1.91-2.13 (1H, m), 2.32 (1H, dq), 3.40 (1H, dd), 3.56-3.72 (2H, m), 3.78 (1H, dd), 4.37 (1H, s), 4.70 (1H, s), 6.78 (1H, dd), 6.98 (1H, dd). m/z: ES$^+$ [M+H]$^+$ 283.

Intermediate 9

2-[3-(Difluoromethoxy)phenyl]-2-(dimethylamino) acetic acid

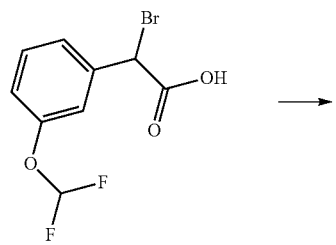
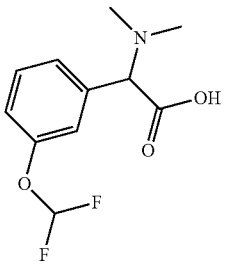

Dimethylamine 2M in THF (0.623 mL, 1.25 mmol) was added to 2-bromo-2-(3-(difluoromethoxy)phenyl)acetic acid (Intermediate 10, 350 mg, 1.25 mmol) and DIPEA (0.665 mL, 3.74 mmol) in MeCN (8 mL) at 21° C. under nitrogen. The resulting mixture was stirred at ambient temperature for 2 hours. The reaction was then evaporated to give crude 2-[3-(difluoromethoxy)phenyl]-2-(dimethylamino)acetic acid as a brown gum which was used crude for subsequent steps; m/z: ES$^+$ [M+H]$^+$ 246.

Intermediate 10

2-Bromo-2-(3-(difluoromethoxy)phenyl)acetic acid

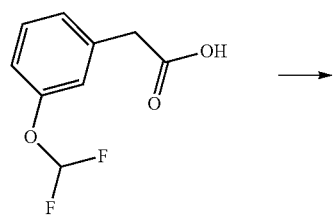

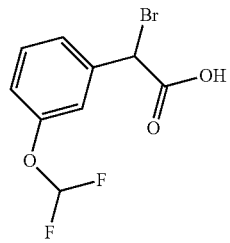

2-(3-(Difluoromethoxy)phenyl)acetic acid (263 mg, 1.30 mmol) and NBS (255 mg, 1.43 mmol) were dissolved in chloroform (10 mL) and heated at 80° C. To this was added (E)-2,2'-(diazene-1,2-diyl)bis(2-methylpropanenitrile) (10.68 mg, 0.07 mmol) and the reaction was stirred at 80° C. for 3 hours. Further NBS was then added (120 mg) and the reaction left refluxing for a further 1.5 hours. The reaction was then left at ambient temperature overnight. Further NBS was added (60 mg) and the reaction heated at 80° C. for a further 1 hour. The reaction was cooled to r.t. and the chloroform removed under reduced pressure leaving crude 2-bromo-2-(3-(difluoromethoxy)phenyl)acetic acid which was used crude in subsequent reactions. m/z: ES$^-$ [M−H]$^-$ 279.

Intermediate 11

2-(Dimethylamino)-2-[3-(trifluoromethoxy)phenyl] acetic acid

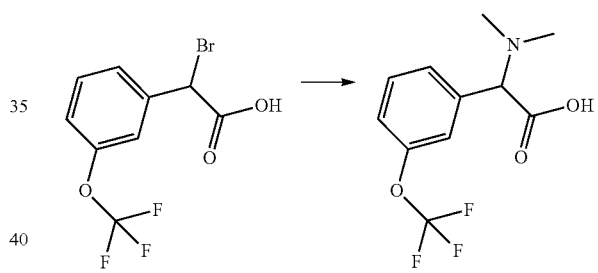

Dimethylamine 2M in THF (7.94 mL, 15.88 mmol) was added to 2-bromo-2-[3-(trifluoromethoxy)phenyl]acetic acid (Intermediate 12, 4.75 g, 15.88 mmol) and DIPEA (8.48 mL, 47.65 mmol) in MeCN (75 mL) at 21° C., giving a slight exotherm. The resulting mixture was stirred at ambient temperature for 2 hours. The reaction was then evaporated to give 2-(dimethylamino)-2-[3-(trifluoromethoxy) phenyl]acetic acid as a brown gum which was used crude in the next step. m/z: ES$^+$ [M+H]$^+$ 264.

Intermediate 12

2-Bromo-2-[3-(trifluoromethoxy)phenyl]acetic acid

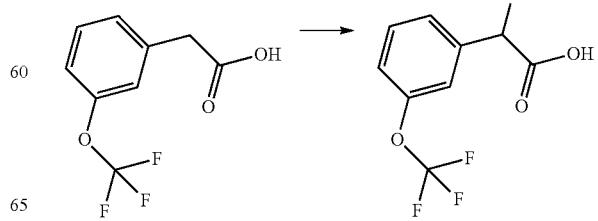

2-(3-(trifluoromethoxy)phenyl)acetic acid (3.5 g, 15.90 mmol) and NBS (3.11 g, 17.49 mmol) were dissolved in chloroform (100 mL) and heated at 80° C. To this was added (E)-2,2'-(diazene-1,2-diyl)bis(2-methylpropanenitrile) (0.131 g, 0.79 mmol) and the reaction was stirred at 80° C. for 6 hours. The reaction was then left at ambient temperature over the weekend. Solvent was then evaporated to give crude 2-bromo-2-[3-(trifluoromethoxy)phenyl]acetic acid which was used without any further purification. m/z: ES+ [M+H]+ 297.

Intermediate 13

2-(Azetidin-1-yl)-2-[3-(difluoromethoxy)phenyl]acetic acid

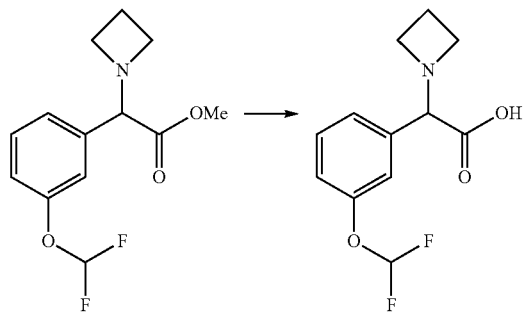 [SMILES: COC(=O)C(c1cccc(OC(F)F)c1)N1CCC1 ; O=C(O)C(c1cccc(OC(F)F)c1)N1CCC1]

A solution of lithium hydroxide monohydrate (96 mg, 2.29 mmol) in water (3 mL) was added to a solution of methyl 2-(azetidin-1-yl)-2-(3-(difluoromethoxy)phenyl)acetate (Intermediate 14, 310 mg, 1.14 mmol) in methanol (6 mL) and the mixture stirred for 18 hours at room temperature. The reaction mixture was then adjusted to pH4 by addition of 2M aqueous HCl. The solution was passed through a 20 g SCX-2 cartridge, eluting with methanol followed by a 1N solution of ammonia in methanol to bring off the product. The solvent was evaporated under reduced pressure to yield 2-(azetidin-1-yl)-2-[3-(difluoromethoxy)phenyl]acetic acid (290 mg, 99%) as a gum; $^1$H NMR (400 MHz, DMSO, 30° C.) δ 2.18 (2H, p), 3.56 (2H, q), 3.75 (2H, q), 4.44 (1H, s), 7.12 (1H, dd), 7.17 (1H, s), 7.20 (1H, t), 7.23 (1H, d), 7.38-7.43 (1H, m); m/z: ES+ [M+H]+ 258.

Intermediate 14

Methyl 2-(azetidin-1-yl)-2-(3-(difluoromethoxy)phenyl)acetate

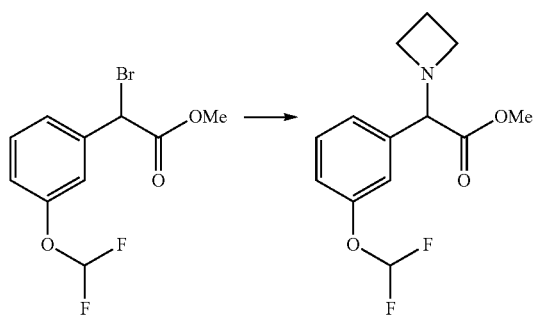 [SMILES: COC(=O)C(Br)c1cccc(OC(F)F)c1 ; COC(=O)C(c1cccc(OC(F)F)c1)N1CCC1]

A solution of triethylamine (263 μl, 1.89 mmol) and azetidine (98 mg, 1.72 mmol) in MeCN (2 mL) was added dropwise to a solution at 0° C. of methyl 2-bromo-2-(3-(difluoromethoxy)phenyl)acetate (Intermediate 15, 507 mg, 1.72 mmol) in MeCN (5 mL). The mixture was stirred for 2 hours at room temperature and then concentrated under reduced pressure. The residue was partitioned between aqueous brine and ethyl acetate, the organic layer was dried (MgSO$_4$), filtered and evaporated under reduced pressure to give methyl 2-(azetidin-1-yl)-2-(3-(difluoromethoxy)phenyl)acetate (310 mg, 67%) as a liquid; $^1$H NMR (400 MHz, CDCl$_3$, 30° C.) δ 2.12 (2H, p), 3.17 (2H, q), 3.28 (2H, q), 3.68 (3H, s), 4.02 (1H, s), 6.52 (1H, t), 7.04-7.08 (1H, m), 7.20 (1H, d), 7.25-7.28 (1H, m), 7.33 (1H, t); m/z: ES+ [M+H]+ 272.

Intermediate 15

Methyl 2-bromo-2-(3-(difluoromethoxy)phenyl)acetate

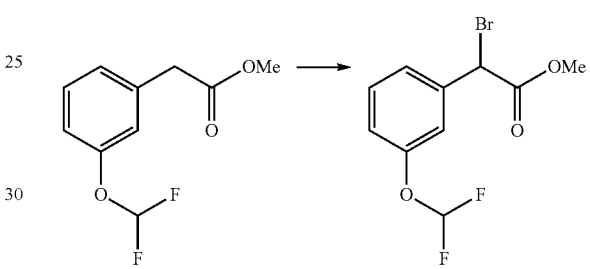

A mixture of methyl 2-(3-(difluoromethoxy)phenyl)acetate (Intermediate 16, 1.1 g, 5.09 mmol) and NBS (0.951 g, 5.34 mmol) and (E)-2,2'-(diazene-1,2-diyl)bis(2-methylpropanenitrile) (0.042 g, 0.25 mmol) in carbon tetrachloride (20 mL) was heated to reflux for 4 hours and then cooled to room temperature. The solid was filtered off and discarded, and the solvent evaporated under reduced pressure. Purification was by flash silica chromatography, (elution gradient 0-5% ethyl acetate in heptane). Fractions containing product were evaporated under reduced pressure to yield methyl 2-bromo-2-(3-(difluoromethoxy)phenyl)acetate (0.830 g, 55%) as a liquid. 1H NMR (400 MHz, CDCl$_3$, 30° C.) δ 3.80 (3H, s), 5.32 (1H, s), 6.52 (1H, t), 7.11 (1H, dt), 7.32-7.4 (3H, m). m/z: GC EI M+ 293.9701.

Intermediate 16

Methyl 2-(3-(difluoromethoxy)phenyl)acetate

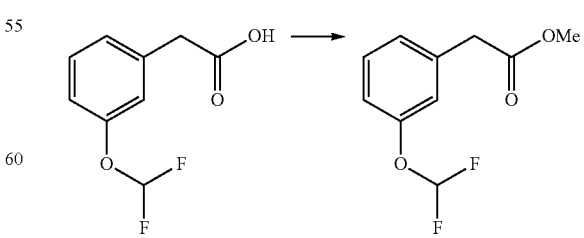

A solution of 2-(3-(difluoromethoxy)phenyl)acetic acid (1 g, 4.95 mmol) and sulfuric acid (10.87 μl, 0.20 mmol) in methanol (30 mL) was refluxed for 2 hours and then cooled to room temperature. The solvent was evaporated under reduced pressure and the residue was partitioned between ethyl acetate and aqueous sodium bicarbonate. The organic layer was dried (MgSO$_4$), filtered and evaporated under reduced pressure to yield methyl 2-(3-(difluoromethoxy)phenyl)acetate (1.1 g, 103%) as an oil. $^1$H NMR (400 MHz, CDCl$_3$, 30° C.) δ 3.63 (2H, s), 3.70 (3H, s), 6.50 (1H, t), 7.01-7.07 (2H, m), 7.11-7.15 (1H, m), 7.31 (1H, t). m/z: GC EI M+ 216.0593.

Intermediate 17

2-(Azetidin-1-yl)-2-(3-methoxyphenyl)acetic acid

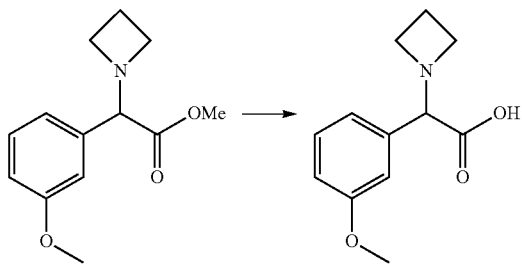 [SMILES: COC(=O)C(c1cccc(OC)c1)N1CCC1 ; COc1cccc(C(C(=O)O)N2CCC2)c1]

A solution of lithium hydroxide (64.1 mg, 2.68 mmol) in water (3 mL) was added to a solution of methyl 2-(azetidin-1-yl)-2-(3-methoxyphenyl)acetate (Intermediate 18, 420 mg, 1.79 mmol) in methanol (6 mL) and the mixture stirred for 18 hours at room temperature. The reaction mixture was then adjusted to pH4 by addition of 2M aqueous HCl. The solution was passed through a 20 g SCX-2 cartridge, eluting with methanol followed by a 1N solution of ammonia in methanol to bring off the product. The solvent was evaporated under reduced pressure to yield 2-(azetidin-1-yl)-2-(3-methoxyphenyl)acetic acid (380 mg, 96%) as a solid; $^1$H NMR (400 MHz, DMSO, 30° C.) δ 2.14-2.24 (2H, m), 3.58 (2H, q), 3.74 (3H, s), 3.79 (2H, q), 4.40 (1H, s), 6.85-6.89 (1H, m), 6.91-6.95 (2H, m), 7.25 (1H, t); m/z: ES$^+$ [M+H]$^+$ 222.

Intermediate 18

Methyl 2-(azetidin-1-yl)-2-(3-methoxyphenyl)acetate

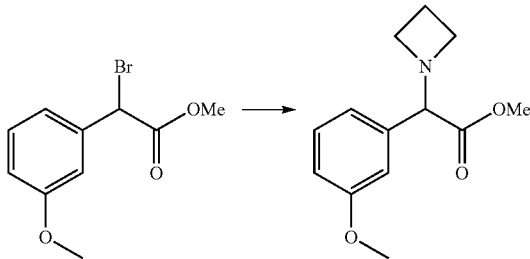 [SMILES: COC(=O)C(Br)c1cccc(OC)c1 ; COC(=O)C(c1cccc(OC)c1)N1CCC1]

A solution of triethylamine (284 μl, 2.04 mmol) and azetidine (106 mg, 1.85 mmol) in acetonitrile (2 mL) was added dropwise to a solution at 0° C. of methyl 2-bromo-2-(3-methoxyphenyl)acetate (Intermediate 19, 480 mg, 1.85 mmol) in MeCN (5 mL). The mixture was stirred for 2 hours at room temperature and then concentrated under reduced pressure. The residue was partitioned between aqueous brine and ethyl acetate, the organic layer was dried (MgSO$_4$), filtered and evaporated under reduced pressure to yield methyl 2-(azetidin-1-yl)-2-(3-methoxyphenyl)acetate (420 mg, 96%) as a liquid; $^1$H NMR (400 MHz, CDCl$_3$, 30° C.) δ 2.11 (2H, p), 3.16 (2H, q), 3.30 (2H, q), 3.67 (3H, s), 3.81 (3H, s), 3.99 (1H, s), 6.82-6.86 (1H, m), 6.96-7 (2H, m), 7.23 (1H, t); m/z: ES$^+$ [M+H]$^+$ 236.

Intermediate 19

Methyl 2-bromo-2-(3-methoxyphenyl)acetate

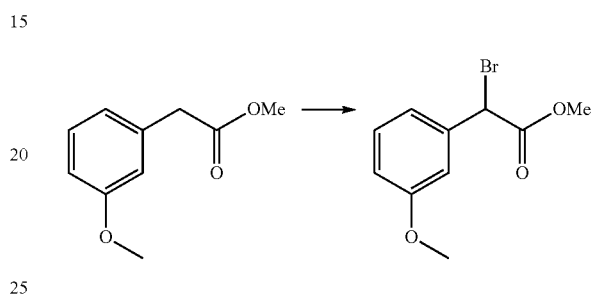

A mixture of methyl 2-(3-methoxyphenyl)acetate (550 mg, 3.05 mmol) and NBS (570 mg, 3.20 mmol) and (E)-2,2'-(diazene-1,2-diyl)bis(2-methylpropanenitrile) (25.06 mg, 0.15 mmol) in carbon tetrachloride (15 mL) was heated to reflux for 4 hours and then cooled to room temperature. The solid was filtered off and discarded, and the solvent evaporated under reduced pressure. Purification was by flash silica chromatography, (elution gradient 0-10% ethyl acetate in heptane). Fractions containing product were evaporated under reduced pressure to yield methyl 2-bromo-2-(3-methoxyphenyl)acetate (490 mg, 62%) as a liquid. $^1$H NMR (400 MHz, CDCl$_3$, 30° C.) δ 3.79 (3H, s), 3.82 (3H, s), 5.33 (1H, s), 6.88 (1H, ddd), 7.07-7.12 (2H, m), 7.23-7.29 (1H, m). m/z: GC EI M+ 257.9882.

Intermediate 20

2-(Azetidin-1-yl)-2-[3-(trifluoromethoxy)phenyl]acetic acid

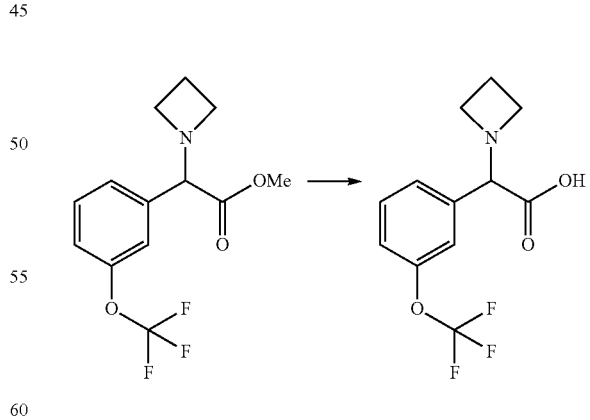

A solution of lithium hydroxide monohydrate (116 mg, 2.77 mmol) in water (3 mL) was added to a solution of methyl 2-(azetidin-1-yl)-2-[3-(trifluoromethoxy)phenyl]acetate (Intermediate 22, 400 mg, 1.38 mmol) in methanol (6 mL) and the mixture stirred for 18 hours at room temperature. The reaction mixture was then adjusted to pH4 by addition of 2M aqueous HCl. The solution was passed through a 20 g SCX-2 cartridge, eluting with methanol followed by a 1N solution of ammonia in methanol to bring off the product. The solvent was evaporated under reduced pressure to 2-(azetidin-1-yl)-2-[3-(trifluoromethoxy)phenyl]acetic acid (380 mg, 100%) as a gum. $^1$H NMR (400 MHz, DMSO, 30° C.) δ 2.19 (2H, p), 3.5-3.6 (2H, m), 3.75 (2H, q), 4.49 (1H, s), 7.31 (1H, d), 7.35 (1H, s), 7.39 (1H, d), 7.50 (1H, t); m/z: ES$^+$ [M+H]$^+$ 276.

Intermediate 21

[2-(azetidin-1-yl)-2-[3-(trifluoromethoxy)phenyl]acetyl]oxylithium

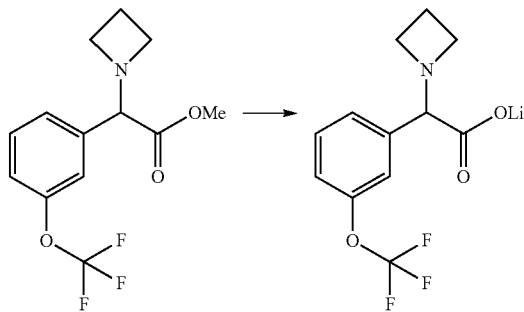

Methyl 2-(azetidin-1-yl)-2-[3-(trifluoromethoxy)phenyl]acetate (Intermediate 22, 0.94 g, 3.25 mmol) and lithium hydroxide monohydrate (0.27 g, 6.5 mmol) were dissolved in a mixture of methanol (10 mL) and water (5 mL). The reaction was stirred for 3 h at r.t. The reaction mixture was evaporated and dried in vacuo to give [2-(azetidin-1-yl)-2-[3-(trifluoromethoxy)phenyl]acetyl]oxylithium as a pale yellow solid (944 mg, 103%).

$^1$H NMR (400 MHz, DMSO-d6) δ 1.79 (p, J=6.9 Hz, 2H) 2.87 (2H, q), 3.01 (2H, q), 3.52 (1H, s), 7.02 (1H, ddt), 7.30-7.20 (3H, m). m/z: ES$^-$ [M+H]$^-$ 275.

Intermediate 22

Methyl 2-(azetidin-1-yl)-2-[3-(trifluoromethoxy)phenyl]acetate

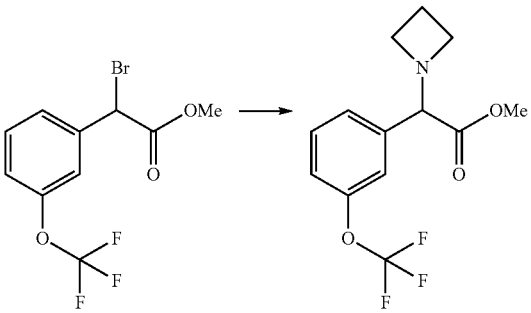 [SMILES: COC(=O)C(Br)c1cccc(OC(F)(F)F)c1 ; COC(=O)C(c1cccc(OC(F)(F)F)c1)N1CCC1]

A solution of fresh azetidine (0.22 mL, 3.19 mmol) and triethylamine (0.49 mL, 3.51 mmol) in MeCN (4 mL) was added dropwise to methyl 2-bromo-2-[3-(trifluoromethoxy)phenyl]acetate (Intermediate 23, 1.0 g, 3.19 mmol) in MeCN (10 mL) cooled in an ice bath under N$_2$. The mixture was allowed to warm to r.t. and stirred for 5 h. The reaction mixture was evaporated to dryness and the residue was partitioned between EtOAc and brine (75 mL each). The organics were dried (MgSO$_4$) and evaporated to give methyl 2-(azetidin-1-yl)-2-[3-(trifluoromethoxy)phenyl]acetate as an orange oil (940 mg, 101%). $^1$H NMR (400 MHz, CDCl$_3$) δ 2.13 (2H, q), 3.17 (2H, td), 3.34-3.24 (2H, m), 3.69 (3H, s), 4.04 (1H, s), 7.16 (1H, m), 7.31 (1H, dq), 7.40-7.33 (2H, m). m/z: ES$^+$ [M+H]$^+$ 290.

Intermediate 23

Methyl 2-bromo-2-[3-(trifluoromethoxy)phenyl]acetate

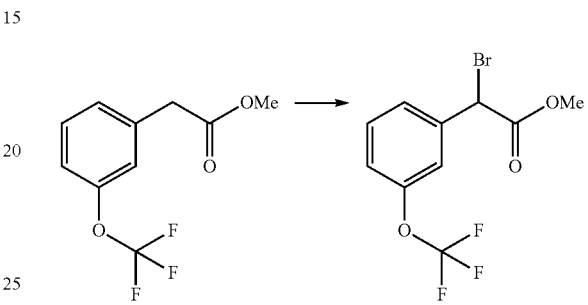

A mixture of methyl 2-[3-(trifluoromethoxy)phenyl]acetate (3.6 g, 15.37 mmol), N-bromosuccinimide (2.87 g, 16.14 mmol) and AIBN (0.13 g, 0.76 mmol) in carbon tetrachloride (50 mL) were heated to reflux for 3 h. It was allowed to cool to room temperature, and the precipitate was removed by filtration through celite. The filtrate was evaporated onto silica and purified by flash column chromatography (SiO$_2$, gradient elution 100% cyclohexane gradually increasing to 10% ethyl acetate in cyclohexane). Pure fractions were evaporated to give methyl 2-bromo-2-[3-(trifluoromethoxy)phenyl]acetate as a pale yellow oil (3.97 g, 82%). $^1$H NMR (400 MHz, CDCl$_3$) δ 3.81 (3H, s), 5.33 (1H, s), 7.22 (1H, ddq), 7.51-7.37 (3H, m).

Intermediate 24

2-Methyl-3,4-dihydro-1H-isoquinoline-1-carboxylic acid, HCl

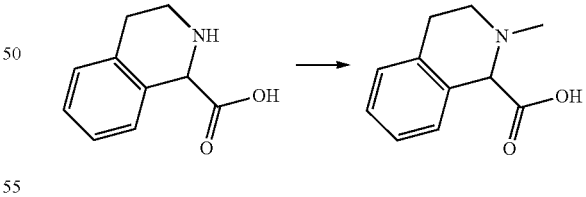

To a suspension of 1,2,3,4-tetrahydroisoquinoline-1-carboxylic acid (Intermediate 25, 2.63 g, 14.84 mmol) in MeOH (150 mL) was added acetic acid (20 mL), hydrochloric acid 6N (2.474 mL, 14.84 mmol), followed by palladium on carbon 10% (350 mg, 3.29 mmol) and formaldehyde (1.506 g, 18.55 mmol). The resulting mixture was stirred at room temperature under a hydrogen atmosphere (balloon) for 18 hours. The catalyst was filtered off and the solvent evaporated under reduced pressure to yield 2-methyl-1,2,3,4-tetrahydroisoquinoline-1-carboxylic acid (3.15 g, 93%) as a solid hydrochloride salt; $^1$H NMR (400 MHz, DMSO, 30° C.) δ 2.89 (3H, s), 3.13 (2H, t), 3.42-3.49

(1H, m), 3.76-3.85 (1H, m), 5.33 (1H, s), 7.27-7.38 (3H, m), 7.41-7.45 (1H, m); m/z: ES+ [M+H]+ 192.

Intermediate 25

1,2,3,4-tetrahydroisoquinoline-1-carboxylic acid

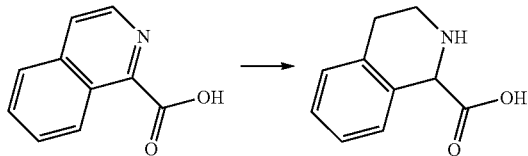 [SMILES: O=C(O)c1nccc2ccccc12 ; O=C(O)C1NCCc2ccccc21]

A 300 mL steel bomb was charged with isoquinoline-1-carboxylic acid (3 g, 17.32 mmol), acetic acid (100 mL) and platinum(IV) oxide (0.2 g, 0.88 mmol). The resulting mixture was hydrogenated at 7 Bar pressure for 18 hours with mechanical stirring. It was diluted with MeOH (80 mL), filtered through celite and rinsed with MeOH and acetic acid. The filtrate was concentrated to dryness go give a light grey solid. Trituration with MeOH gave 1,2,3,4-tetrahydroisoquinoline-1-carboxylic acid (2.63 g, 86%) as a light grey solid that was used without any further purification.

Intermediate 26

(2S)-2-(Dimethylamino)-2-(4-methylphenyl)acetic acid

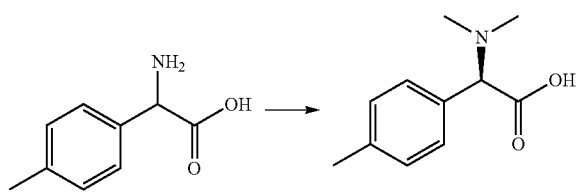

Into a 1-L round-bottom flask purged and maintained with an inert atmosphere of nitrogen, was placed 2-amino-2-(p-tolyl)acetic acid (36 g, 217.93 mmol, 1.00 equiv), hydrogen chloride (120 mL, 1N, 3.95 mol, 18.10 equiv), methanol (120 mL, 2.96 mol, 13.60 equiv), Paraformaldehyde (37% in $H_2O$, 120 mL) and palladium on carbon (36 g, 338.28 mmol, 1.60 equiv). The resulting solution was stirred for 48 h at room temperature under an atmosphere of hydrogen (balloon). The solids were filtered off and the filtrate was concentrated under vacuum. The resulting solution was diluted with 1500 mL of methanol. The pH value of the solution was adjusted to 6 with MeONa. The solids were filtered off and the resulting filtrate was concentrated under vacuum. The crude product was purified by preparatory SFC (column, CHIRALPAK AD-H SFC, 5×25 cm, 5 m; mobile phase, $CO_2$ (55%), MEOH (0.2% DEA)(45%); Detector, UV 220 nm. This resulted in (2S)-2-(dimethylamino)-2-(p-tolyl)acetic acid (10 g, 24%) as a white solid; $^1$H NMR (300 MHz, $CD_3OD$, 25° C.) δ 2.32 (3H, s), 2.60 (6H, s), 7.19-7.21 (2H, d), 4.22 (1H, s), 7.37-7.40 (2H, d); m/z: ES+ [M+H]+ 194.

Intermediate 27

(2S)-2-(Dimethylamino)-2-(3-methylphenyl)acetic acid

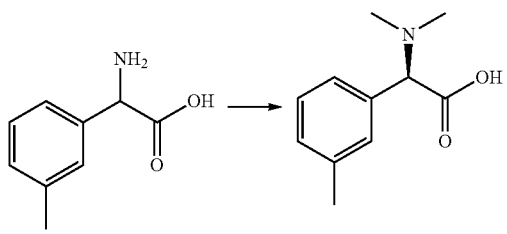

Into a 1-L round-bottom flask purged and maintained with an inert atmosphere of nitrogen, was placed 2-amino-2-(4-methylphenyl)acetic acid (36 g, 217.93 mmol, 1.00 equiv), hydrogen chloride (120 mL, 1 N, 2.60 mol, 12.00 equiv), methanol (120 mL, 2.96 mol, 13.60 equiv), Paraformaldehyde (37% in $H_2O$, 120 mL) and palladium on carbon (36 g, 338.28 mmol, 1.60 equiv). The resulting solution was stirred for 48 h at room temperature under an atmosphere of hydrogen (balloon). The solids were filtered off and the filtrate was concentrated under vacuum. The resulting solution was diluted with methanol (1500 mL). The pH value of the solution was adjusted to 6 with MeONa. The solids were filtered off and the resulting filtrate was concentrated under vacuum. The crude product was purified by preparatory SFC (column, CHIRALPAK AD-H SFC, 5×25 cm, 5 μm); mobile phase, $CO_2$ (60%), MEOH (0.2% DEA)(40%); detector, UV 220 nm. This resulted in (2S)-2-(dimethylamino)-2-(3-methylphenyl)acetic acid (10 g, 24%) as a white solid; $^1$H NMR (300 MHz, $CD_3OD$, 27° C.) δ 2.37 (3H, s), 2.62 (6H, s), 4.20 (1H, s), 7.21-7.38 (4H, m); m/z: ES+ [M+H]+ 194.

Intermediate 28

[2-(Azetidin-1-yl)-2-[4-fluoro-3-(trifluoromethoxy)phenyl]acetyl]oxylithium

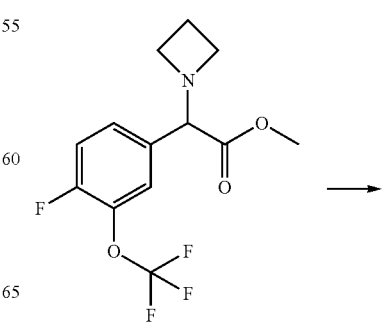

-continued

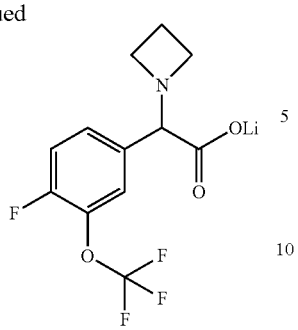

Methyl 2-(azetidin-1-yl)-2-(3-methoxyphenyl)acetate (Intermediate 29, 0.76 g, 3.25 mmol) and lithium hydroxide monohydrate (0.1 g, 2.49 mmol) were dissolved in a mixture of methanol (5 mL) and water (2 mL). The reaction was stirred for 2 h at r.t then evaporated under reduced pressure and dried in vacuo over the weekend to give [2-(azetidin-1-yl)-2-[4-fluoro-3-(trifluoromethoxy)phenyl]acetyl]oxylithium as a pale yellow solid (0.48 g, 97%).

$^1$H NMR (400 MHz, DMSO-d6) δ 1.72 (2H, p) 2.80 (2H, q), 2.93 (2H, q), 3.44 (1H, s), 7.16 (1H, dd), 7.24 (1H, ddd), 7.34 (1H, dt). m/z: ES$^-$ [M–H]$^-$ 294.

Intermediate 29

Methyl 2-(azetidin-1-yl)-2-[4-fluoro-3-(trifluoromethoxy)phenyl]acetate

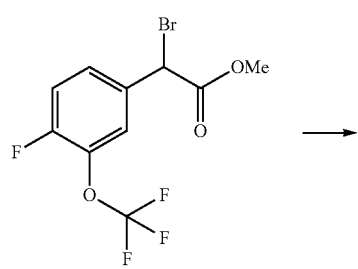

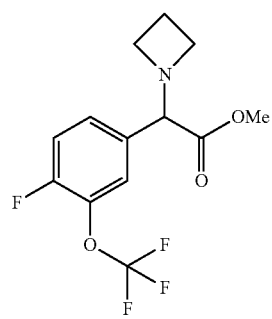

A solution of fresh azetidine (0.12 mL, 1.81 mmol) and triethylamine (0.28 mL, 1.99 mmol) in MeCN (5 mL) was added dropwise to methyl 2-bromo-2-[4-fluoro-3-(trifluoromethoxy)phenyl]acetate (Intermediate 30, 0.6 g, 1.812 mmol) in MeCN (12 mL) cooled in an ice bath under N$_2$. The mixture was allowed to warm to r.t. and stirred for 2 h. The reaction mixture was evaporated to dryness and the residue was partitioned between EtOAc and brine (100 mL each). The organics were dried (MgSO$_4$) and evaporated to give methyl 2-(azetidin-1-yl)-2-[4-fluoro-3-(trifluoromethoxy)phenyl]acetate as a yellow gum (0.51 g, 93%).

$^1$H NMR (400 MHz, CDCl$_3$) δ 2.14 (2H, q) 3.17 (2H, td), 3.27 (2H, td), 3.69 (3H, s), 4.00 (1H, s), 7.20-7.14 (1H, m), 7.35 (1H, dddd), 7.43 (1H, ddd). m/z: ES$^+$ [M+H]$^+$ 308.

Intermediate 30

Methyl 2-bromo-2-[4-fluoro-3-(trifluoromethoxy)phenyl]acetate

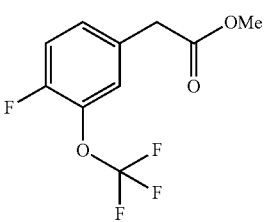

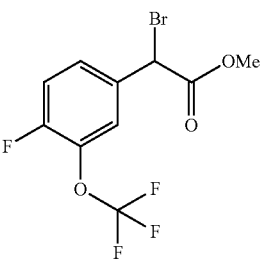

Methyl 2-[4-fluoro-3-(trifluoromethoxy)phenyl]acetate (Intermediate 31, 0.65 g, 2.578 mmol) and N-bromosuccinimide (4.08 g, 22.919 mmol) were weighed into a round bottomed flask and 2,2-azobis(2-methylpropionitrile), (AIBN, 0.02 g, 0.129 mmol) in carbon tetrachloride (6 mL) were added. The reaction was heated to reflux for 4 hours and allowed to cool to room temperature. The precipitate was filtered off and the solution was treated with silica and evaporated under reduced pressure and was purified by flash column chromatography eluting with 100% cyclohexane gradually increasing to 30% EtOAc in cyclohexane. Appropriate fractions were evaporated under reduced pressure to yield methyl 2-bromo-2-[4-fluoro-3-(trifluoromethoxy)phenyl]acetate as a pale yellow oil (1.1 g, 129%).

$^1$H NMR (400 MHz, CDCl$_3$, 25° C.) δ 3.81 (3H, s), 5.29 (1H, s), 7.17-7.24 (1H, m,), 7.46-7.52 (1H, m), 7.53-7.59 (1H, m).

Intermediate 31

Methyl 2-[4-fluoro-3-(trifluoromethoxy)phenyl]acetate

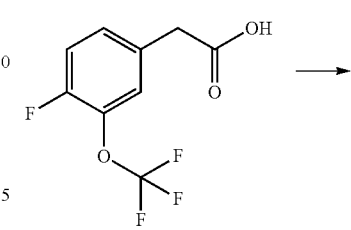

-continued

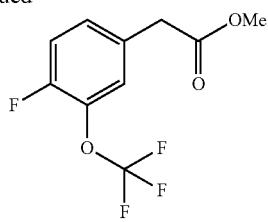

4-Fluoro-3-(trifluoromethoxy)phenylacetic acid (1.0 g, 4.199 mmol) was suspended in methanol (10 mL) and treated with sulfuric acid (0.07 mL, 0.84 mmol) and heated at 45° C. for 2 hours. The reaction mixture was allowed to cool to room temperature and the methanol removed under reduced pressure. The residue was diluted with brine (20 mL) and then extracted with EtOAc (3×20 mL). The combined EtOAc extracts were washed with brine (30 mL) dried over MgSO$_4$, filtered and the solvent was removed under reduced pressure to yield methyl 2-[4-fluoro-3-(trifluoromethoxy)phenyl]acetate (0.65 g, 61%). $^1$H NMR (400 MHz, DMSO-d6) δ 3.63 (3H, s), 3.78 (2H, s), 7.33-7.39 (1H, m), 7.42-7.53 (2H, m). m/z: ES$^+$ [M+H]$^+$ 253.

Intermediate 32

(2S)-2-(3-Cyanophenyl)-2-(dimethylamino)acetic acid

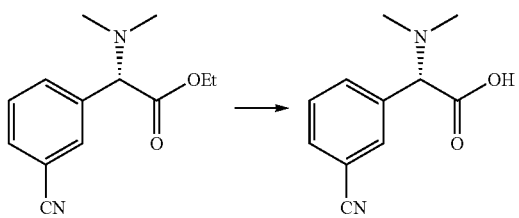 [SMILES: CCOC(=O)[C@H](c1cccc(C#N)c1)N(C)C ; CN(C)[C@H](C(=O)O)c1cccc(C#N)c1]

Into a 500-mL 3-necked round-bottom flask, was placed a solution of ethyl (2S)-2-(3-cyanophenyl)-2-(dimethylamino)acetate (Intermediate 33, 18 g, 77.49 mmol, 1.00 equiv) in tetrahydrofuran (200 mL) and a solution of LiOH (3.56 g, 148.66 mmol, 2.00 equiv) in water (100 mL). The resulting solution was stirred for 3 h at 25° C. The resulting solution was extracted with 2×100 mL of dichloromethane and the organic layers combined. The pH value of the solution was adjusted to 3-4 with aqueous hydrogen chloride (1 mol/L). The resulting mixture was concentrated under vacuum. The resulting mixture was washed with 2×100 mL of acetone. This resulted in 15 g (95%) of (2S)-2-(3-cyanophenyl)-2-(dimethylamino)acetic acid as a white solid. $^1$H NMR (400 MHz, DMSO-d6) δ 2.46 (6H, s), 4.28 (1H, s), 7.61-7.58 (1H, t), 7.77-7.75 (1H, d), 7.86-7.81 (2H, t). m/z: ES$^+$ [M+H]$^+$ 205.

Intermediate 33

Ethyl (2S)-2-(3-cyanophenyl)-2-(dimethylamino) acetate

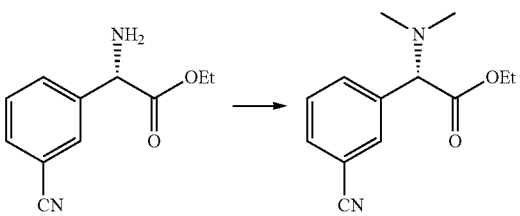 [SMILES: CCOC(=O)[C@@H](N)c1cccc(C#N)c1 ; CCOC(=O)[C@H](c1cccc(C#N)c1)N(C)C]

Into a 1000-mL 3-necked round-bottom flask, was placed a solution of ethyl (2S)-2-amino-2-(3-cyanophenyl)acetate (Intermediate 34, 20 g, 97.93 mmol, 1.00 equiv) in methanol (200 mL), a solution of formaldehyde (44.1 g, 1.47 mol, 6.00 equiv) in water and NaBH$_3$CN (18.2 g, 289.62 mmol, 3.00 equiv). The resulting solution was stirred overnight at 25° C. The resulting mixture was concentrated under vacuum. The residue was applied onto a silica gel column with ethyl acetate/petroleum ether (1/1). This resulted in 18 g (79%) of ethyl (2S)-2-(3-cyanophenyl)-2-(dimethylamino)acetate as a white solid.

Intermediate 34

Ethyl (2S)-2-amino-2-(3-cyanophenyl)acetate

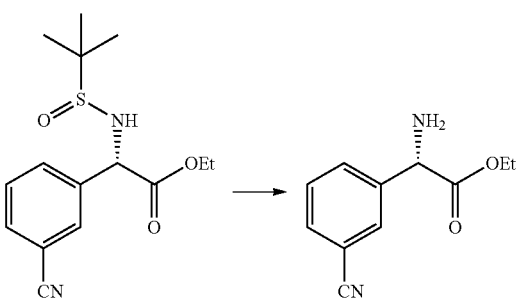 [SMILES: CCOC(=O)[C@@H](NS(=O)C(C)(C)C)c1cccc(C#N)c1 ; CCOC(=O)[C@@H](N)c1cccc(C#N)c1]

Into a 1000-mL 3-necked round-bottom flask, was placed a solution of ethyl (2S)-2-(3-cyanophenyl)-2-[(2-methylpropane-2-sulfinyl)amino]acetate (Intermediate 35, 40.00 g, 129.70 mmol, 1.00 equiv) in 1,4-dioxane (100 mL) and a solution of hydrogen chloride (g) in 1,4-dioxane (200 mL). The resulting solution was stirred overnight at 25° C. The resulting mixture was concentrated under vacuum. The resulting mixture was washed with 1×100 mL of MTBE. This resulted in 20 g (76%) of ethyl (2S)-2-amino-2-(3-cyanophenyl)acetate as a light yellow solid.

Intermediate 35

(2S)-2-(3-Cyanophenyl)-2-[(2-methylpropane-2-sulfinyl)amino]acetate

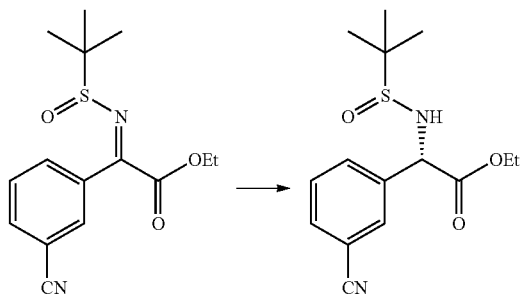 [SMILES: CCOC(=O)/C(=N/S(=O)C(C)(C)C)c1cccc(C#N)c1 ; CCOC(=O)[C@@H](NS(=O)C(C)(C)C)c1cccc(C#N)c1]

Into a 2000-mL 4-necked round-bottom flask, was placed a solution of ethyl (2Z)-2-(3-cyanophenyl)-2-[[(S)-2-methylpropane-2-sulfinyl]imino]acetate (Intermediate 36, 50 g, 163.20 mmol, 1.00 equiv) in tetrahydrofuran (1000 mL). This was followed by the addition of L-selectride (196 mL, 917.61 mmol, 1.20 equiv) dropwise with stirring at −78° C. The resulting solution was stirred for 5 h at −78° C. The reaction was then quenched by the addition of 500 mL of aqueous NH$_4$Cl. The resulting solution was extracted with 3×350 mL of ethyl acetate and the organic layers combined. The resulting mixture was washed with 1×200 mL of brine. The mixture was dried over anhydrous sodium sulfate and concentrated under vacuum. This resulted in 40 g (79%) of ethyl (2S)-2-(3-cyanophenyl)-2-[(2-methylpropane-2-sulfinyl)amino]acetate as yellow oil.

Intermediate 36

Ethyl (2Z)-2-(3-cyanophenyl)-2-[[(S)-2-methylpropane-2-sulfinyl]imino]acetate

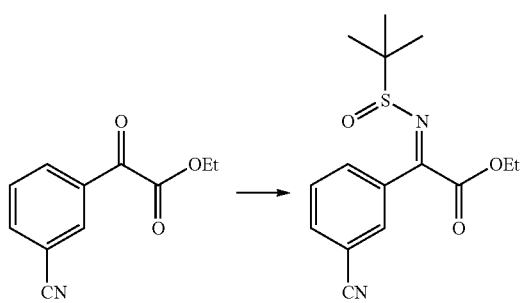 [SMILES: CCOC(=O)C(=O)c1cccc(C#N)c1 ; CCOC(=O)/C(=N/S(=O)C(C)(C)C)c1cccc(C#N)c1]

Into a 3000-mL 4-necked round-bottom flask, was placed a solution of ethyl 2-(3-cyanophenyl)-2-oxoacetate (Intermediate 37, 80 g, 393.71 mmol, 1.00 equiv) in tetrahydrofuran (800 mL), (S)-2-methylpropane-2-sulfinamide (52.5 g, 433.16 mmol, 1.10 equiv) and tetraethoxytitanium (134.7 g, 590.51 mmol, 1.50 equiv). The resulting solution was stirred overnight at 65° C. The reaction was then quenched by the addition of 200 mL of NaCl.aq. The solids were filtered out. The resulting solution was extracted with 3×250 mL of ethyl acetate and the organic layers combined. The resulting mixture was washed with 1×200 mL of brine. The mixture was dried over anhydrous sodium sulfate and concentrated under vacuum. The residue was applied onto a silica gel column and eluted with ethyl acetate/petroleum ether (1/2). This resulted in 50 g (41%) of ethyl (2Z)-2-(3-cyanophenyl)-2-[[(S)-2-methylpropane-2-sulfinyl]imino]acetate as yellow oil.

Intermediate 37

Ethyl 2-(3-cyanophenyl)-2-oxoacetate

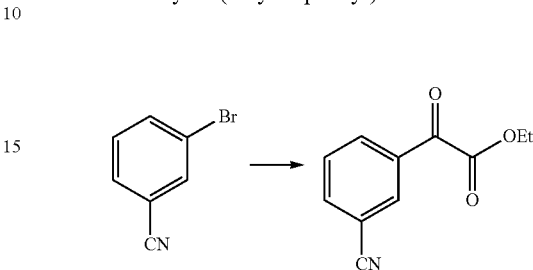

Into a 5000-mL 4-necked round-bottom flask purged and maintained with an inert atmosphere of nitrogen, was placed a solution of 3-bromobenzonitrile (200 g, 1.10 mol, 1.00 equiv) in tetrahydrofuran (1000 mL). This was followed by the addition of i-PrMgCl (663 mL, 5.38 mol, 1.20 equiv) dropwise with stirring at 0° C. The resulting solution was stirred for 2 h at 0° C. To this was added diethyl oxalate (193.6 g, 1.32 mol, 1.20 equiv) dropwise with stirring at −40° C. The resulting solution was stirred for 1 h at −40° C. The reaction was then quenched by the addition of 800 mL of HCl. The resulting mixture was concentrated under vacuum. The pH value of the solution was adjusted to 8-9 with sodium bicarbonate. The resulting solution was extracted with 3×500 mL of ethyl acetate and the organic layers combined and dried over anhydrous sodium sulfate and concentrated under vacuum. The residue was applied onto a silica gel column eluting with ethyl acetate/petroleum ether (1/1). This resulted in 80 g (36%) of ethyl 2-(3-cyanophenyl)-2-oxoacetate as yellow oil.

Intermediate 38

(2R)-2-(Dimethylamino)-2-[3-(trifluoromethoxy)phenyl]acetic acid

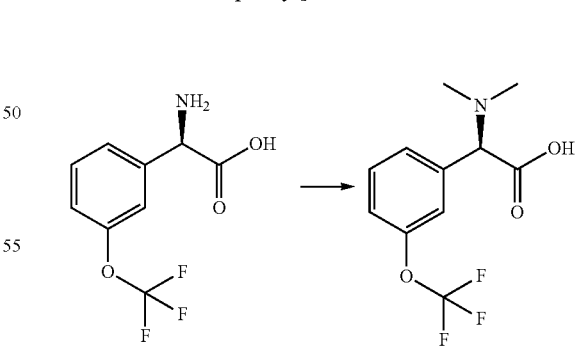

(2R)-2-amino-2-[3-(trifluoromethoxy)phenyl]acetic acid (1 g, 4.25 mmol), formaldehyde (1.277 g, 42.52 mmol) and Pd—C(0.045 g, 0.43 mmol) in MeOH (30 mL) and hydrochloric acid, (1N) (2 mL) was stirred under an atmosphere of hydrogen at pressure and 40° C. for 16 hours. The reaction mixture was filtered through celite. The solid was washed with MeOH (20 mL). The filtrate were combined and evaporated to afford (2S)-2-(dimethylamino)-2-[3-(trifluoromethoxy)phenyl]acetic acid (1 g, 89%) as a white solid; m/z: ES+ [M+H]+ 264.

Intermediate 39

(2S)-2-(Dimethylamino)-2-[3-(trifluoromethoxy)phenyl]acetic acid

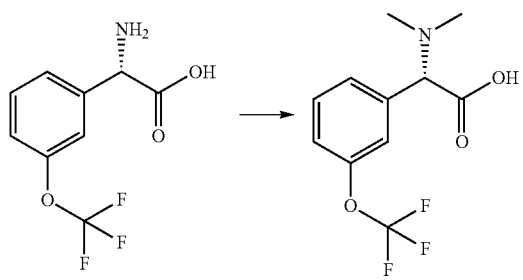 [SMILES: N[C@H](C(=O)O)c1cccc(OC(F)(F)F)c1 ; CN(C)[C@H](C(=O)O)c1cccc(OC(F)(F)F)c1]

(2S)-2-amino-2-[3-(trifluoromethoxy)phenyl]acetic acid (1 g, 4.25 mmol), formaldehyde (1.277 g, 42.52 mmol) and Pd—C(0.045 g, 0.43 mmol) in MeOH (30 mL) and hydrochloric acid, (1N) (2 mL) was stirred under an atmosphere of hydrogen at pressure and 40° C. for 16 hours. The reaction mixture was filtered through celite. The solid was washed with MeOH (20 mL). The filtrate were combined and evaporated to afford (2R)-2-(dimethylamino)-2-[3-(trifluoromethoxy)phenyl]acetic acid (1 g, 89%) as a white solid; m/z: ES+ [M+H]+ 264.

Biological Assays

The following assays were used to measure the effects of the compounds described herein: a) GLS Enzyme Potency Assay; b) GLS Cell Potency Assay; c) GLS Cell Proliferation Assay. During the description of the assays, generally:
 i. The following abbreviations have been used: $CO_2$=Carbon dioxide; DMEM=Dulbecco's Modified Eagle Medium; DMSO=Dimethyl sulphoxide; EDTA=Ethylenediaminetetraacetic acid; EGTA=Ethylene glycol tetraacetic acid; FCS=Foetal calf serum; h=Hour(s); NBS=Non-binding surface; SDS=Sodium dodecyl sulphate; TRIS=Tris(Hydroxymethyl)aminomethane.
 ii. $IC_{50}$ values were calculated using a smart fitting model in Genedata. The $IC_{50}$ value was the concentration of test compound that inhibited 50% of biological activity.

Assay a): GLS Enzyme Potency Assay

A Glutamate Oxidase/AmplexRed coupled assay was used to measure the ability of compounds to bind to and inhibit the activity of GLS1 in vitro. 6His tagged GLS protein (amino acids 63-669) expressed in *E. Coli* was purified and stored at −80° C. in aliquots. GLS1 was diluted to 2×working concentration and incubated at room temperature to allow the tetrameric/dimeric forms to reach steady state. Assay measurements were performed in buffer comprising 50 mM TRIS pH 7.8, 100 mM $NaPO_4$, pH 7.8, 0.001% v/v Tween20. Purified recombinant GLS1 protein was diluted in assay buffer to 12 nM and pre-incubated at room temperature for 30 minutes. Test compounds were prepared by dilution in 100% DMSO to give the correct dose range for 12 point concentration response and an appropriate volume (2.5-60 nl) dispensed into 384 well micro assay plates (Greiner product code 784900) using a Labcyte Echo 555 acoustic dispenser. DMSO concentration was maintained at 2% by back filling with DMSO solution. 3 μL of diluted GLS1 protein (12 nM) was then dispensed into each well using a BioRaptr automated dispenser (Beckman-Coulter) and incubated for 15 minutes at room temperature. 3 μL of 100 mM glutamine diluted in assay buffer was then added and the reaction incubated at room temperature for 60 minutes. The reaction was then stopped by addition of 45 μM 6-(2-bromoethynyl)-2,3-dimethyl-quinazolin-4-one, 75 μM Amplex Red, 0.375 units/mL Horseradish Peroxidase, 0.12 units/mL Glutamate Oxidase in 100 mM TRIS pH7.5. After 30 minutes at room temp in the dark, plates were read on a Perkin Elmer EnVision using 535/590 nm optic filters and raw data analysed using Genedata to generate $IC_{50}$ values. An artefact version of the assay where the 6His tagged GLS protein and glutamine were replaced with assay buffer was also used to rule out non specific effects on the assay components.

Assay b): GLS Cell Potency Assay

Compounds were assessed for their potential to inhibit cellular GLS activity by use of a PC3 coupled assay measuring cellular glutamate depletion. Test compounds were prepared by dilution in 100% DMSO to give the correct dose range for 12 point concentration response and an appropriate volume (5-120 nl) dispensed into 384 well micro assay plates (Corning product code 3712) using a Labcyte Echo 555 acoustic dispenser. DMSO concentration was maintained at 0.3% by back filling with DMSO solution. PC3 cells were grown in phenol free DMEM, 10% dialyzed FCS, 2 mM glutamine and following dispersal by trypsinisation were plated at $5.6 \times 10^3$ cells per well in 40 μl of growth medium directly into the 384 well assay plates containing dispensed compound. After incubation for 6 h at 37° C., 5% $CO_2$ growth media was aspirated and cells lysed in 15 μl of buffer containing 10 mM TRIS pH7.4, 100 mM NaCl, 1 mM EDTA, 1 mM EGTA, 1 mM NaF, 20 mM $Na_4P_2O_7$, 2 mM $Na_3VO_4$, 1% Triton X-100, 10% glycerol, 0.1% SDS and 0.5% deoxycholate. 4 μl Of cell lysate was then transferred to a 384 well NBS plate (Corning product code 3575) and 35 μl of 27.5 M Amplex Red, 0.1375 U/mL Horseradish Peroxidase, 0.044 U/mL glutamate oxidase, 100 mM TRIS pH7.5 was added. After 30 minutes at room temp in the dark, plates were read on a Perkin Elmer EnVision using 535/590 nm optic filters and raw data analysed using proprietary software to generate $IC_{50}$ values.

Assay c): GLS Cell Proliferation Assay

The ability of compounds to inhibit cell growth was measured using a 384 well plate NCI-H1703 cell proliferation assay. NCI-H1703 cells were grown in phenol red free RPMI1640, 10% FCS and 2 mM glutamine and seeded at a density of 750 cells per well in 40 μl of growth medium into clear-bottom 384 well assay plates (Corning product code 3712) and incubated for 24 h at 37° C., 5% $CO_2$. Test compounds were prepared by dilution in 100% DMSO to give the correct dose range for 12 point concentration response and an appropriate volume (5-120 nl) dispensed directly into the assay plates containing plated cells. DMSO concentration was maintained at 0.3% by back filling with DMSO solution. Plates were incubated for 5 days at 37° C., 5% $CO_2$, Sytox Green and Saponin added to final concentration of 2 μM and 0.25% respectively and incubated for 6 h prior to analysis. Plates were read on an Acumen eX3 (TTP Labtech) using 488 nm excitation and FITC filter set (500-530 nm) for emission. $IC_{50}$ values were calculated by curve fitting to max inhibition of day zero growth using GeneData software analysis.

Results from assays a)-c) are shown in Table 1.

TABLE 1

Assay data

| Compound Example # | Assay a) enzyme IC$_{50}$ µM | Assay b) GLS cell MOA Mean IC$_{50}$ µM | Assay c) Prolif Mean IC$_{50}$ µM |
|---|---|---|---|
| 1(a) | 1.72 | 0.0334 | 0.0686 |
| 1(b) | 0.0826 | 0.00408 | 0.0547 |
| 2(a) | 0.0746 | 0.00344 | 0.0896 |
| 2(b) | 1.24 | 0.0128 | 0.0979 |
| 3(a) | 0.261 | 0.0112 | 0.0127 |
| 3(b) | 0.0524 | 0.000295 | 0.00825 |
| 4(a) | 0.0564 | 0.000405 | 0.00841 |
| 4(b) | 0.522 | 0.00191 | 0.00252 |
| 5(a) | 0.981 | 0.022 | 0.0293 |
| 5(b) | 0.0772 | 0.00192 | 0.0132 |
| 6(a) | 0.981 | 0.022 | 0.0293 |
| 6(b) | 0.944 | 0.0297 | 0.0808 |
| 7(a) | 1.33 | 0.00861 | 0.00624 |
| 7(b) | 0.102 | 0.000985 | 0.00245 |
| 8(a) | 0.053 | 0.00191 | 0.00881 |
| 8(b) | 0.194 | 0.0209 | 0.0851 |
| 9 | 0.132 | 0.00281 | 0.0448 |
| 10 | 0.0592 | 0.00212 | 0.0212 |
| 11(a) | 0.952 | 0.0308– | 0.0191 |
| 11(b) | 0.132 | 0.00177– | 0.0301 |
| 12(a) | 2.51 | 0.0153 | 0.0116 |
| 12(b) | 0.246 | 0.00141 | 0.0129 |
| 13 | 0.226 | 0.0113 | 0.0768 |
| 14 | 2.26 | 0.0102 | 0.00523 |
| 15 | 3.75 | 0.0222 | 0.152 |
| 16 | 0.198 | 0.00476 | 0.131 |
| 17 | 0.187 | 0.0107 | 0.163 |
| 18 | 0.182 | 0.0011 | 0.00351 |

The invention claimed is:

1. A compound of Formula (I):

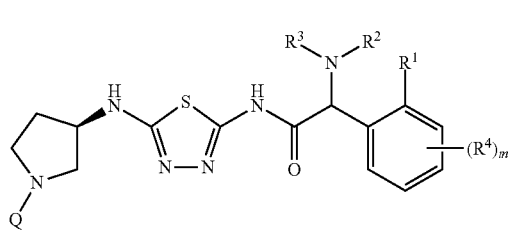

or a pharmaceutically acceptable salt thereof, wherein:
Q is pyridazin-3-yl, or 6-fluoropyridazin-3-yl;
$R^1$ is H;
$R^2$ and $R^3$ are each independently C1-C6 alkyl, or $R^2$ and $R^3$ taken together are —(CH$_2$)$_3$—;
or $R^1$ and $R^2$ taken together are —(CH$_2$)$_2$— and $R^3$ is —CH$_3$;
$R^4$ is halo, —CH$_3$, —OCH$_3$, —OCHF$_2$, —OCF$_3$, or —CN; and
n is 0, 1, or 2.

2. The compound of claim 1, or a pharmaceutically acceptable salt thereof, wherein Q is pyridazin-3-yl.

3. The compound of claim 1, or a pharmaceutically acceptable salt thereof, wherein n is 0.

4. The compound of claim 1, or a pharmaceutically acceptable salt thereof, wherein n is 1 and $R^4$ is methyl, methoxy, difluoromethoxy, trifluoromethoxy, and cyano, and $R^4$ is at the 3-position.

5. The compound of claim 1, or a pharmaceutically acceptable salt thereof, wherein n is 1 and $R^4$ is selected from the group consisting of fluoro and methyl and $R^4$ is at the 4-position.

6. The compound of claim 1, or a pharmaceutically acceptable salt thereof, wherein n is 2, one instance of $R^4$ is trifluoromethoxy and is at the 3-position, and the other instance of $R^4$ is fluoro and is at the 4-position.

7. The compound of claim 1, or a pharmaceutically acceptable salt thereof, wherein $R^2$ and $R^3$ are each independently methyl.

8. The compound of claim 1, or a pharmaceutically acceptable salt thereof, wherein $R^2$ and $R^3$ taken together are —(CH$_2$)$_3$—.

9. The compound of claim 1, or a pharmaceutically acceptable salt thereof, wherein $R^1$ is H.

10. The compound of claim 1, or a pharmaceutically acceptable salt thereof, wherein $R^1$ and $R^2$ taken together are —(CH$_2$)$_2$— and $R^3$ is —CH$_3$.

11. The compound of claim 1, or a pharmaceutically acceptable salt thereof, wherein the compound is selected from the group consisting of:
(2S)-2-(dimethylamino)-2-phenyl-N-[5-[[(3R)-1-pyridazin-3-ylpyrrolidin-3-yl]amino]-1,3,4-thiadiazol-2-yl]acetamide;
(2R)-2-(dimethylamino)-2-phenyl-N-[5-[[(3R)-1-pyridazin-3-ylpyrrolidin-3-yl]amino]-1,3,4-thiadiazol-2-yl]acetamide;
(2S)-2-(dimethylamino)-2-(4-fluorophenyl)-N-[5-[[(3R)-1-pyridazin-3-ylpyrrolidin-3-yl]amino]-1,3,4-thiadiazol-2-yl]acetamide;
(2R)-2-(dimethylamino)-2-(4-fluorophenyl)-N-[5-[[(3R)-1-pyridazin-3-ylpyrrolidin-3-yl]amino]-1,3,4-thiadiazol-2-yl]acetamide;
(2S)-2-[3-(difluoromethoxy)phenyl]-2-(dimethylamino)-N-[5-[[(3R)-1-pyridazin-3-ylpyrrolidin-3-yl]amino]-1,3,4-thiadiazol-2-yl]acetamide;
(2R)-2-[3-(difluoromethoxy)phenyl]-2-(dimethylamino)-N-[5-[[(3R)-1-pyridazin-3-ylpyrrolidin-3-yl]amino]-1,3,4-thiadiazol-2-yl]acetamide;
(2S)-2-(dimethylamino)-N-[5-[[(3R)-1-pyridazin-3-ylpyrrolidin-3-yl]amino]-1,3,4-thiadiazol-2-yl]-2-[3-(trifluoromethoxy)phenyl]acetamide;
(2R)-2-(dimethylamino)-N-[5-[[(3R)-1-pyridazin-3-ylpyrrolidin-3-yl]amino]-1,3,4-thiadiazol-2-yl]-2-[3-(trifluoromethoxy)phenyl]acetamide;
(2S)-2-(azetidin-1-yl)-2-[3-(difluoromethoxy)phenyl]-N-[5-[[(3R)-1-pyridazin-3-ylpyrrolidin-3-yl]amino]-1,3,4-thiadiazol-2-yl]acetamide;
(2R)-2-(azetidin-1-yl)-2-[3-(difluoromethoxy)phenyl]-N-[5-[[(3R)-1-pyridazin-3-ylpyrrolidin-3-yl]amino]-1,3,4-thiadiazol-2-yl]acetamide;
(2S)-2-(azetidin-1-yl)-2-(3-methoxyphenyl)-N-[5-[[(3R)-1-pyridazin-3-ylpyrrolidin-3-yl]amino]-1,3,4-thiadiazol-2-yl]acetamide;
(2R)-2-(azetidin-1-yl)-2-(3-methoxyphenyl)-N-[5-[[(3R)-1-pyridazin-3-ylpyrrolidin-3-yl]amino]-1,3,4-thiadiazol-2-yl]acetamide;
(2S)-2-(azetidin-1-yl)-N-[5-[[(3R)-1-pyridazin-3-ylpyrrolidin-3-yl]amino]-1,3,4-thiadiazol-2-yl]-2-[3-(trifluoromethoxy)phenyl]acetamide;
(2R)-2-(azetidin-1-yl)-N-[5-[[(3R)-1-pyridazin-3-ylpyrrolidin-3-yl]amino]-1,3,4-thiadiazol-2-yl]-2-[3-(trifluoromethoxy)phenyl]acetamide;
(1S)-2-methyl-N-[5-[[(3R)-1-pyridazin-3-ylpyrrolidin-3-yl]amino]-1,3,4-thiadiazol-2-yl]-3,4-dihydro-1H-isoquinoline-1-carboxamide;

(1R)-2-methyl-N-[5-[[(3R)-1-pyridazin-3-ylpyrrolidin-3-yl]amino]-1,3,4-thiadiazol-2-yl]-3,4-dihydro-1H-isoquinoline-1-carboxamide;

(2S)-2-(dimethylamino)-2-(p-tolyl)-N-[5-[[(3R)-1-pyridazin-3-ylpyrrolidin-3-yl]amino]-1,3,4-thiadiazol-2-yl]acetamide;

(2S)-2-(dimethylamino)-2-(m-tolyl)-N-[5-[[(3R)-1-pyridazin-3-ylpyrrolidin-3-yl]amino]-1,3,4-thiadiazol-2-yl]acetamide;

(2S)-2-(Azetidin-1-yl)-2-[4-fluoro-3-(trifluoromethoxy)phenyl]-N-[5-[[(3R)-1-pyridazin-3-ylpyrrolidin-3-yl]amino]-1,3,4-thiadiazol-2-yl]acetamide;

(2R)-2-(Azetidin-1-yl)-2-[4-fluoro-3-(trifluoromethoxy)phenyl]-N-[5-[[(3R)-1-pyridazin-3-ylpyrrolidin-3-yl]amino]-1,3,4-thiadiazol-2-yl]acetamide;

(2S)-2-(azetidin-1-yl)-N-[5-[[(3R)-1-(6-fluoropyridazin-3-yl)pyrrolidin-3-yl]amino]-1,3,4-thiadiazol-2-yl]-2-[3-(trifluoromethoxy)phenyl]acetamide;

(2R)-2-(azetidin-1-yl)-N-[5-[[(3R)-1-(6-fluoropyridazin-3-yl)pyrrolidin-3-yl]amino]-1,3,4-thiadiazol-2-yl]-2-[3-(trifluoromethoxy)phenyl]acetamide; and (2S)-2-(3-cyanophenyl)-2-(dimethylamino)-N-[5-[[(3R)-1-pyridazin-3-ylpyrrolidin-3-yl]amino]-1,3,4-thiadiazol-2-yl]acetamide.

12. The compound of claim 1, or a pharmaceutically acceptable salt thereof, wherein the compound is selected from the group consisting of:

(2S)-2-(dimethylamino)-2-phenyl-N-[5-[[(3R)-1-pyridazin-3-ylpyrrolidin-3-yl]amino]-1,3,4-thiadiazol-2-yl]acetamide;

(2S)-2-(dimethylamino)-2-(4-fluorophenyl)-N-[5-[[(3R)-1-pyridazin-3-ylpyrrolidin-3-yl]amino]-1,3,4-thiadiazol-2-yl]acetamide;

(2R)-2-[3-(difluoromethoxy)phenyl]-2-(dimethylamino)-N-[5-[[(3R)-1-pyridazin-3-ylpyrrolidin-3-yl]amino]-1,3,4-thiadiazol-2-yl]acetamide;

(2S)-2-[3-(difluoromethoxy)phenyl]-2-(dimethylamino)-N-[5-[[(3R)-1-pyridazin-3-ylpyrrolidin-3-yl]amino]-1,3,4-thiadiazol-2-yl]acetamide;

(2S)-2-(dimethylamino)-N-[5-[[(3R)-1-pyridazin-3-ylpyrrolidin-3-yl]amino]-1,3,4-thiadiazol-2-yl]-2-[3-(trifluoromethoxy)phenyl]acetamide;

(2S)-2-(azetidin-1-yl)-2-[3-(difluoromethoxy)phenyl]-N-[5-[[(3R)-1-pyridazin-3-ylpyrrolidin-3-yl]amino]-1,3,4-thiadiazol-2-yl]acetamide;

(2S)-2-(azetidin-1-yl)-2-(3-methoxyphenyl)-N-[5-[[(3R)-1-pyridazin-3-ylpyrrolidin-3-yl]amino]-1,3,4-thiadiazol-2-yl]acetamide;

(2S)-2-(azetidin-1-yl)-N-[5-[[(3R)-1-pyridazin-3-ylpyrrolidin-3-yl]amino]-1,3,4-thiadiazol-2-yl]-2-[3-(trifluoromethoxy)phenyl]acetamide;

(1S)-2-methyl-N-[5-[[(3R)-1-pyridazin-3-ylpyrrolidin-3-yl]amino]-1,3,4-thiadiazol-2-yl]-3,4-dihydro-1H-isoquinoline-1-carboxamide;

(2S)-2-(dimethylamino)-2-(p-tolyl)-N-[5-[[(3R)-1-pyridazin-3-ylpyrrolidin-3-yl]amino]-1,3,4-thiadiazol-2-yl]acetamide;

(2S)-2-(dimethylamino)-2-(m-tolyl)-N-[5-[[(3R)-1-pyridazin-3-ylpyrrolidin-3-yl]amino]-1,3,4-thiadiazol-2-yl]acetamide;

(2S)-2-(azetidin-1-yl)-2-[4-fluoro-3-(trifluoromethoxy)phenyl]-N-[5-[[(3R)-1-pyridazin-3-ylpyrrolidin-3-yl]amino]-1,3,4-thiadiazol-2-yl]acetamide;

(2S)-2-(azetidin-1-yl)-N-[5-[[(3R)-1-(6-fluoropyridazin-3-yl)pyrrolidin-3-yl]amino]-1,3,4-thiadiazol-2-yl]-2-[3-(trifluoromethoxy)phenyl]acetamide;

(2R)-2-(azetidin-1-yl)-N-[5-[[(3R)-1-(6-fluoropyridazin-3-yl)pyrrolidin-3-yl]amino]-1,3,4-thiadiazol-2-yl]-2-[3-(trifluoromethoxy)phenyl]acetamide; and (2S)-2-(3-cyanophenyl)-2-(dimethylamino)-N-[5-[[(3R)-1-pyridazin-3-ylpyrrolidin-3-yl]amino]-1,3,4-thiadiazol-2-yl]acetamide.

13. A pharmaceutical composition comprising the compound of claim 1, or a pharmaceutically acceptable salt thereof, and at least one pharmaceutically acceptable diluent or carrier.

14. The compound of claim 1, or a pharmaceutically acceptable salt thereof, for use in the treatment of cancer.

15. A method for treating cancer in a warm-blooded animal having said cancer, comprising administering to the warm-blooded animal a therapeutically effective amount of the compound of claim 1, or a pharmaceutically acceptable salt thereof.

16. The method according to claim 15, wherein the cancer is breast cancer, lung cancer, pancreatic cancer, renal cancer, or hepatocellular cancer.

* * * * *